(12) United States Patent
Kanai et al.

(10) Patent No.: US 7,422,561 B2
(45) Date of Patent: Sep. 9, 2008

(54) ULTRASONOGRAPHIC SYSTEM AND ULTRASONOGRAPHY

(75) Inventors: Hiroshi Kanai, Sendai (JP); Yoshiro Koiwa, Sendai (JP); Motonao Tanaka, Sendai (JP)

(73) Assignee: Japan Science and Technology Agency, Saitama (JP)

( * ) Notice: Subject to any disclaimer, the term of this patent is extended or adjusted under 35 U.S.C. 154(b) by 367 days.

(21) Appl. No.: 10/507,381

(22) PCT Filed: Sep. 4, 2002

(86) PCT No.: PCT/JP02/08975

§ 371 (c)(1), (2), (4) Date: Sep. 9, 2004

(87) PCT Pub. No.: WO03/077765

PCT Pub. Date: Sep. 25, 2003

(65) Prior Publication Data

US 2005/0124881 A1   Jun. 9, 2005

(30) Foreign Application Priority Data

Mar. 18, 2002   (JP) ............................. 2002-074957

(51) Int. Cl.
*A61B 8/00* (2006.01)
(52) U.S. Cl. ................. 600/437; 600/438; 600/450
(58) Field of Classification Search ................. 600/437, 600/442, 440, 438, 449, 450, 508; 382/128
See application file for complete search history.

(56) References Cited

U.S. PATENT DOCUMENTS

| | | | |
|---|---|---|---|
| 4,217,909 A | * | 8/1980 | Papadofrangakis et al. .. 600/441 |
| 4,470,303 A | | 9/1984 | O'Donnell |
| 4,688,428 A | | 8/1987 | Nicolas |
| 4,803,994 A | * | 2/1989 | Burke .......................... 600/442 |
| 4,867,167 A | | 9/1989 | Magnin |
| 5,097,836 A | | 3/1992 | Yamada et al. |
| 5,840,028 A | | 11/1998 | Chubachi et al. |

FOREIGN PATENT DOCUMENTS

EP    0 383 288    8/1990

(Continued)

OTHER PUBLICATIONS

Kanai et al., filed Jul. 1997, *Noninvasive Evaluation of Local Myocardial Thickening and Its Color-Coded Imaging*, IEEE Transactions on Ultrasonics, Ferroelectrics, and Frequency Control, vol. 44, No. 4, Jul. 1997.

(Continued)

*Primary Examiner*—Eric F Winakur
*Assistant Examiner*—Katherine L Fernandez
(74) *Attorney, Agent, or Firm*—McGlew & Tuttle, P.C.

(57) ABSTRACT

An ultrasonic diagnostic system prepares a diagnostic data including image by transmitting ultrasonic pulses to a living tissue, and receiving and analyzing reflected wave of the ultrasonic pulses, and has an analytical processing unit to measure a backscattering intensity by using a scattering wave from a region of interest in the living tissue on a basis of the reflected wave which is received, and to detect a variation frequency of the measured backscattering intensity to obtain the diagnostic data to be available.

9 Claims, 18 Drawing Sheets

FOREIGN PATENT DOCUMENTS

| | | |
|---|---|---|
| JP | 1-98982 | 4/1989 |
| JP | 2-215448 | 8/1990 |
| JP | 5-337111 | 12/1993 |
| JP | 10-5226 | 1/1998 |
| JP | 2000-152929 | 6/2000 |
| JP | 2000-229078 | 8/2000 |

OTHER PUBLICATIONS

Hasegawa et al., 1998, *Accuracy Evaluation in the Measurement of a Small Change in the Thickness of Arterial Walls and the Measurement of Elasticity of the Human Carotid Artery,* Jpn. J. Appl. Phys. vol. 37, (1998) pp. 3101-3105.

Kanai et al. Sep. 1999, *Real-Time Measurements of Local Myocardium Motion and Arterial Wall Thickening,* IEEE Transactions on Ultrasonics, Ferroelectrics, and Frequency Control, vol. 46, No. 5, Sep. 1999.

Katsumata et al., Sep. 2001, *Measurement of Rapid Variation in Ultrasound Integrated Backscatter from Heart Wall during a Cardiac Cycle,* The Institute of Electronics, Information and Communication Engineers, Sep. 2001.

\* cited by examiner

ULTRASONOGRAPHIC SYSTEM AND ULTRASONOGRAPHY

BACKGROUND OF THE INVENTION

1. Field of the Invention

This invention relates to an ultrasonic diagnostic system and an ultrasonic diagnostic method, and more particularly to an ultrasonic diagnostic system and an ultrasonic diagnostic method which enable a lesion on a living tissue, such as the heart, to be diagnosed by a noninvasive measurement using ultrasonic, by which local degeneration of myocardial structure in any region of the heart wall is identified, visually displayed and thereby enabled to be diagnosed.

2. Description of the Related Art

In diagnosing heart diseases due to the malfunctioning of cardiac muscle, such as hypertrophic cardiomyopathy, dilated cardiomyopathy or ischemic cardiac diseases including myocardial infarction, the tissue characteristics of cardiac muscle should be identified. While known methods include diagnosis using ultrasonic integrated backscatter besides invasive biopsy, available diagnostic apparatuses cannot follow variations in the region of interest, because they fix the region of interest in the heart wall. Accordingly these apparatuses can mainly sense signals of around 1 Hz due to density variations of myocardial fibers, but can hardly diagnose structural changes in cardiac muscle. The present invention is intended to provide an effective solution to this problem.

Diagnosis of Heart Diseases:

Ultrasonic diagnostic methods for heart diseases extensively used today are mostly based on morphological aspects of the heart, such as evaluation of its wall thickness or the cardiac output, but can hardly be helpful in the tissue characterization of cardiac muscle. Although it is essential to know the tissue characteristics of cardiac muscle in diagnosing heart diseases including hypertrophic cardiomyopathy, dilated cardiomyopathy and ischemic cardiac diseases such as myocardial infarction, tissue characterization of cardiac muscle requires biopsy of cardiac muscle. Since this is an invasive technique, it imposes heavy physical and mental burdens on the subject, and therefore cannot be repetitively applied. On account of these background circumstances, there is a keen call for a noninvasive tissue characterization method applicable to cardiac muscle.

It is already known that observation of a heart suspected of obsolete myocardial infarction or dilated cardiomyopathy by a B-mode image or an M-mode image gives high brightness of echoes, namely high intensity of ultrasonic reflected, from the heart wall. However, it is difficult to quantitatively assess it on the image.

On the other hand, ultrasonic integrated backscatter (IB) from the heart wall is attracting note as a promising evaluation method for quantitative tissue characterization of the heart. Ultrasonic IB is measured as an average reflective power of ultrasonic from a given region in the tissue. The intensity of IB from the heart wall is known to manifest cyclic variations (CV) matching the pulsation of the heart, falling in the systole and rising in the diastole. Studies have been made on such cyclic variations of IB from many different aspects.

Physiology of Cardiac Muscle:

The mesh structure (or network structure) of fascicles of cardiac muscle fibers (each of about 50 fibers) finely varies between the systole and the diastole. The honeycomb-liked network structure, comprising lozenge units, is pulled in the diastole to crush each lozenge in shape. This changes the inclination of the face reflecting the ultrasonic. As the lozenges are crushed in the diastole, the ultrasonic coming vertically on the cardiac muscle fibers are more readily scattered, resulting in an increased backscattering intensity. In the systole on the other hand, each lozenge recovers its original full shape, and the inclination of the face reflecting the ultrasonic coming vertically on the cardiac muscle fibers is increased to make it more difficult for the ultrasonic to be scattered, resulting in a decrease of backscattering intensity IB.

There are clinical reports that the amplitude of the CV of IB is smaller in a patient of a cardiac disease such as myocardial infarction, hypertrophic cardiomyopathy or dilated cardiomyopathy than in a healthy person and the baseline of the ultrasonic backscatter IB is higher. Regarding this CV of IB, Hete et al., measuring the IB from extracted chicken skeletal muscle, demonstrated that the IB intensity rose when the muscle was passively extended, and attributed variations in IB level due to the extension of muscle to changes in the orientation of intercellular substance. Wickline et al., measuring the IB from the heart wall of a dog subjected to thoracotomy, studied the physical characteristics of the cardiac muscle by using a three-element Maxwell model. Their conclusion was that that the cardiac CV of IB could be attributed to variations in acoustic impedance accompanying the extension and contraction of the cardiac muscle.

Principle of Measurement of IB from Heart Wall:

The ultrasonic backscatter IB can be calculated by [Equation 1] below as the average power of ultrasonic reflected by a given region in the depthwise direction in the object.

$$IB_0(t) = 10\log_{10} \frac{1}{\Delta D(t)} \int_{D_0(t)}^{D_0(t)+\Delta D(t)} |z(t,D)|^2 \, dD \quad \text{[Equation 1]}$$

Here, z(t, D) is the orthogonal detection signal of the reflected signal, $D_o(t)$ the distance of ultrasonic propagation to the region of interest (ROI) at time t, and $\Delta D(t)$ the width of ROI.

FIG. 18 schematically illustrates an IB measuring system. A region of interest (ROI) 22 is set in a heart wall 21. Ultrasonic is transmitted from an ultrasonic probe 23 to the heart wall 21 at a repetition cycle of $\Delta T$. The resultant reflected signal is detected with an orthogonal detector 24. The orthogonal detection signal z (t, D) thereby obtained is subjected to amplitude squaring. And, the time signal $IB_o(t)$ of the IB value is obtained by integrating with an integrator 25 the signal portions at different points of time from the region of interest (ROI) 22 according to [Equation 1] above.

In the measurement of IB from the heart wall in the scenes of medical practice today, dozens of frames of B-mode tomograms are taken, and the examiner sets the position of ROI in each frame to obtain the IB. However, as the heart wall moves translationally along with pulsation, and the wall thickness varies with the myocardial extension and contraction, the position and size of the ROI should be varied from one point of time to another, and therefore it is difficult by this method to measure the IB from the same region of the heart wall all the time.

Ultrasonic Integrated Backscatter from Cardiac Muscle:

Ultrasonic integrated backscatter IB from cardiac muscle is known to cyclically vary along with the pulsation of the heart (varying at a low frequency of about 1 Hz as the heart pulsates about once per second). In recent years, the function to measure such cyclic variations has come to be incorporated into ultrasonic diagnosing apparatuses for general medical purposes as well, and used for the tissue characterization of cardiac muscle. As cardiac muscle relaxes and extends in the diastole and contracts in the systole, (1) the number of cardiac muscle fibers (the number of scatterers) per unit volume varies (the density of cardiac muscle fibers varies) and at the same time (2) the intensity of the integrated backscatter also varies along with structural changes of cardiac muscle (for conventional methods of integrated backscatter, see References 1 through 4).

However, as the size and position of the region of interest set in the heart wall is assumed to be invariable during one beat for the expedience of the processing of calculation in IB measurements conducted with conventional ultrasonic diagnosing apparatuses (see for References 1 and 2), in effect the sum of the density variation under (1) and the intensity variation of the integrated backscatter within the region of interest under (2) ((1) +(2)) is measured. Of these factors, the density variation under (1) is 30% less in the systole than in the diastole, and this corresponds to 10 dB in scattering wave power. In such a conventional IB measurement, the density variation can be considered the dominant factor. Therefore, by the convention technique, only the variation in the density of scatterers within the region of interest is measured.

Phased Tracking Method:

Viewed from the aspect of high precision measurement of a blood vessel disease for instance, the conventional echocardiography M-mode has a resolution of only 1 mm or so at most. Similarly, when the vibration of an aorta is determined as a displacement velocity by the conventional Doppler method, the conditions for accuracy are satisfied theoretically, but the pulsation of the blood vessel has so significant an influence that it is difficult to extract a minute vibration superimposed over this relatively large amplitude. In view of this difficulty, researchers including the present inventors developed a phased tracking method whereby such a minute vibration on the beating heart or large blood vessel would be remotely measured ultrasonically to enable the elasticity modulus of the blood vessel wall on any selected spot could be calculated. Thus it was made possible to accurately diagnose the susceptibility of the content of an atheroma to rupture (see References 5 through 10). This phased tracking method will be outlined below.

The phased tracking method is a new bioinstrumentation for measuring minute vibration velocities of the heart wall and the blood vessel wall. It makes possible accurate measurement of vibrations of 500 Hz or less and 0.01 mm and changes of the wall in the order of 10 microns. By this method, for instance, minute velocities at a plurality of measurement points positioned between the intramural layers or on the wall of an artery by the ultrasonic Doppler method, and the minute velocities at the measurement points are subjected to time integral thereby to calculate positional changes over time at the measurement points. Since positional changes over time at the measurement points reveal variations in layer thickness, from which the elasticity modulus of the layer can be measured, it is made possible to estimate the susceptibility to rupture (Reference 6).

In practice, as shown in FIG. 19, measurement point (i) is set in the wall of an artery on an ultrasonic beam 26, and measurement point (i+1) is set in the next depth. Then, the minute vibration velocities $v_i(t)$ and $v_{i+1}(t)$ are measured for the measurement points, and the differences between the two velocities are subjected to time integral, thereby thickness change $\Delta h(t)$ is determined which is thickness change of the layer between the measuring points (i) and (i+1) in the arterial wall. Incidentally, reference numeral 27 denotes plaques.

The References are listed below.
1. U.S. Pat. No. 4,867,167
2. U.S. Pat. No. 4,803,994
3. U.S. Pat. No. 4,688,428
4. U.S. Pat. No. 4,470,303
5. Japanese Patent Gazette (Patent Laid-Open No. 10-5226)
6. Japanese Patent Gazette (Patent Laid-Open No. 2000-229078)
7. U.S. Pat. No. 5,840,028
8. Kanai, H., Hasegawa, H., Chubachi, N., Koiwa, Y. and Tanaka, M., "Noninvasive evaluation of local myocardial thickness in heart wall and its color coding", IEEE transaction UFFC, 1997; 44:752-768
9. Hasegawa., H, Kanai., H, Hoshimiya., N, Chubachi, N., Koiwa, Y., "Accuracy evaluation in the measurement of a small change in the thickness of arterial walls and the measurement of elasticity of the human calotid artery", Jpn. J. Appl. Phys. 1998; 37:3101-3105
10. Kanai, H., Koiwa, Y., Zhang J., "Real-time measurements of local myocardium motion and arterial wall thickening", IEEE transaction UFFC, 1999; 46:1229-1241

Earlier studies on ultrasonic backscatter IB took note only of the difference between the maximum and the minimum of IB in one cardiac cycle, but paid no sufficient attention to the variation of the IB value at each point of time in one cardiac cycle.

SUMMARY OF THE INVENTION

It is an object of the present invention to provide an ultrasonic diagnostic system that is capable of acquiring detailed information on local tissue characteristics of cardiac muscle by utilizing ultrasonic backscatter IB with a view to more accurate diagnosis of heart diseases.

It is another object of the invention to provide an ultrasonic diagnostic method that permits acquisition of detailed information on local tissue characteristics of cardiac muscle by utilizing ultrasonic backscatter IB with a view to more accurate diagnosis of heart diseases.

An ultrasonic diagnostic system and an ultrasonic diagnostic method can have any of the structures described below.

The ultrasonic diagnostic system of the present invention prepares a diagnostic data including image by transmitting ultrasonic pulses to a living tissue, and receives and analyzes reflected wave of the ultrasonic pulses, and comprises an analytical processing unit to measure a backscattering intensity by using a scattering wave from a region of interest in the living tissue on a basis of the reflected wave which is received, and to detect a variation frequency of the measured backscattering intensity to obtain the diagnostic data to be available.

Preferably, in the ultrasonic diagnostic system described above, the ultrasonic pulses are transmitted at a high repeated transmission frequency of a few kHz to measure the backscattering intensity.

Preferably, in the ultrasonic diagnostic system described above, the analytical processing unit further comprises means for calculating a displacement waveform of the region of interest by applying a phased tracking method to the reflected wave signal which is received.

Preferably, in the ultrasonic diagnostic system described above, the analytical processing unit further comprises means for calculating the backscattering intensity on the displacement waveform of the region of interest calculated by applying the phased tracking method.

Preferably, in the ultrasonic diagnostic system described above, the analytical processing unit further comprises means for detecting the variation frequency or the variation cycle of the calculated backscattering intensity.

Preferably, in the ultrasonic diagnostic system described above, the variation frequency of the backscattering intensity is a frequency of tens to hundreds of Hz.

Preferably, in the ultrasonic diagnostic system described above, the analytical processing unit further comprises means for displaying in an assessable manner the instantaneous thickness variation velocity of the region of interest on the basis of the variation frequency or the variation cycle of the detected backscattering intensity.

Preferably, in the ultrasonic diagnostic system described above, the means for displaying has a function to convert the variation frequency or the variation cycle of the backscattering intensity of the region of interest into a suitable color or a density level according to a predetermined color bar or gray scale, and to display it in the converted form on a screen.

Preferably, in the ultrasonic diagnostic system described above, the function to display on the screen is to display superimposed over an M-mode image the value of the variation frequency or the variation cycle of the backscattering intensity converted into a color or a density level.

An ultrasonic diagnostic method prepares a diagnostic data including image by transmitting ultrasonic pulses to a living tissue, and receives and analyzes reflected wave of the ultrasonic pulses, and comprises measuring a backscattering intensity by using a scattering wave from a region of interest in the living tissue on a basis of the reflected wave which is received, and detecting a variation frequency of the measured backscattering intensity to obtain the diagnostic data to be available.

Preferably, in the ultrasonic diagnostic method described above, the ultrasonic pulses are transmitted at a high repeated transmission frequency of a few kHz to measure the backscattering intensity.

Preferably, in the ultrasonic diagnostic method described above, the displacement waveform of the region of interest is calculated by applying a phased tracking method to the reflected wave signal which is received.

Preferably, in the ultrasonic diagnostic method described above, the backscattering intensity is calculated on the displacement waveform of the region of interest calculated by applying the phased tracking method.

Preferably, in the ultrasonic diagnostic method described above, the variation frequency or the variation cycle of the calculated backscattering intensity is detected.

Preferably, in the ultrasonic diagnostic method described above, the variation frequency of the backscattering intensity is a frequency of tens to hundreds of Hz.

Preferably, in the ultrasonic diagnostic method described above, the instantaneous thickness variation velocity of the region of interest is displayed in an assessable manner on the basis of the variation frequency or the variation cycle of the detected backscattering intensity.

Preferably, in the ultrasonic diagnostic method described above, the variation frequency or the variation cycle of the backscattering intensity of the region of interest is converted into a suitable color or a density level according to a predetermined color bar or gray scale and is displayed in the converted form on a screen, in order to display in an assessable manner the instantaneous thickness variation velocity of the region of interest.

Preferably, in the ultrasonic diagnostic method described above, the value of the variation frequency or the variation cycle of the backscattering intensity converted into a color or a density level is displayed by superimposing over an M-mode image.

DETAILED DESCRIPTION OF THE PREFERRED EMBODIMENT

We earlier measured ultrasonic integrated backscatter IB from the heart wall of a healthy person at a repeated transmission frequency of a few kHz, and discovered, in addition to the already known CV synchronized with the heart beat, a component varying at a frequency of tens to hundreds of Hz superimposed over the CV. The present invention is made on the basis of this finding, and makes it possible to obtain the average power of IB from the region of interest by measuring the ultrasonic integrated backscatter IB at a high repeated transmission frequency of a few kHz, and to supply that variation frequency or variable cycle for displaying.

Figure 1:
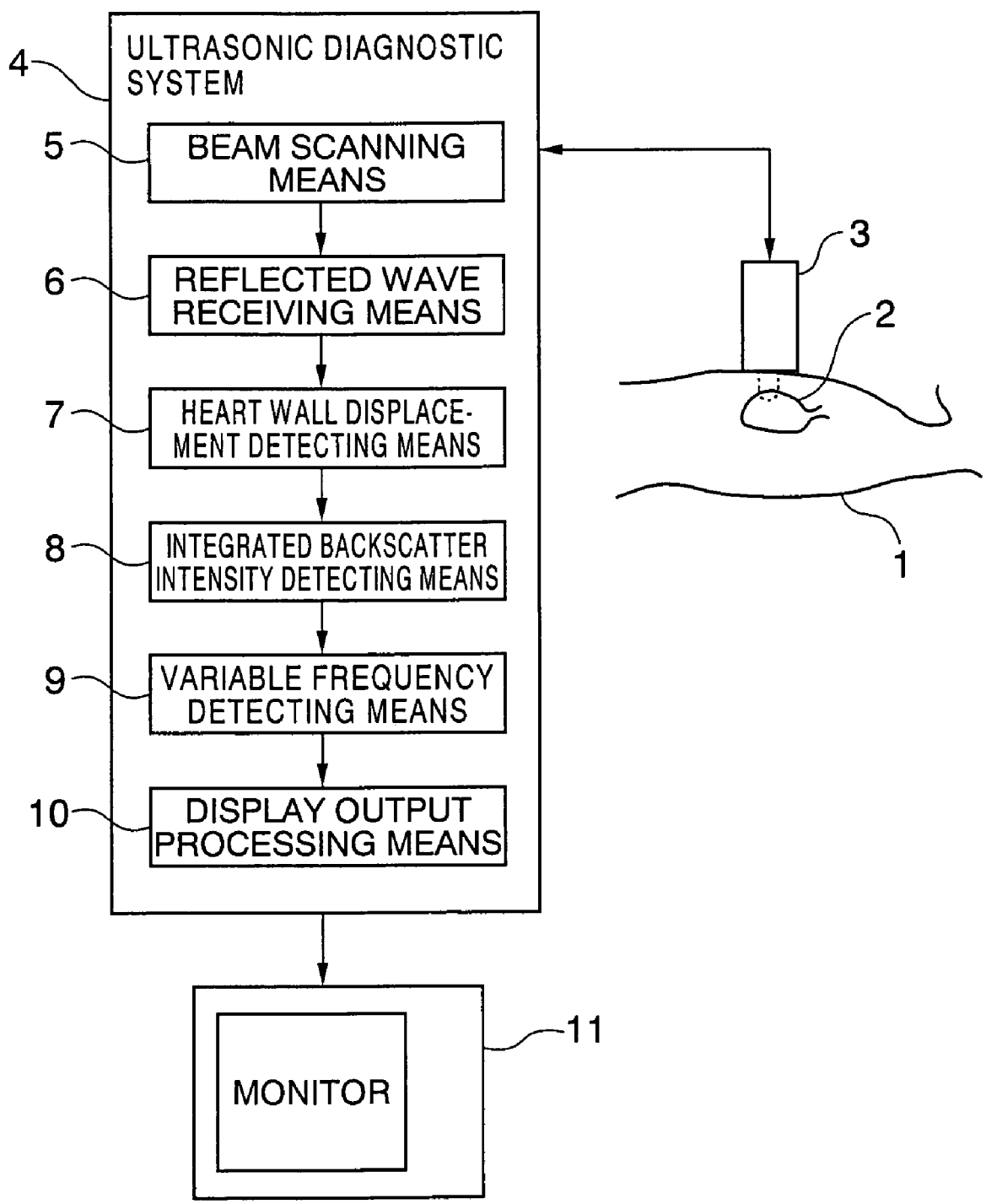
FIG. 1 schematically shows an ultrasonic diagnostic system according to the present invention.

FIG. 1 schematically shows an ultrasonic diagnostic system according to the present invention. In FIG. 1, the object of diagnosis is the heart 2 of a subject 1. An ultrasonic pulse is transmitted from the body surface of the subject 1 by using an ultrasonic probe 3, and its reflected wave is received. An ultrasonic diagnostic system 4 according to invention controls the beam scanning of the ultrasonic pulse transmission, analyzes the received reflected wave signal to prepare a diagnostic image such as a tomogram, and displays it on a monitor 11. Main functions constituting the ultrasonic diagnostic system 4 are shown in the blocks of means 5 through 10. Beam scanning means 5 transmits the ultrasonic pulse while successively changing over the radiating position of an ultrasonic beam. In the case of the present invention, the ultrasonic pulse is transmitted at a repetition frequency of a few kHz especially to enhance the time-resolution. Reflected wave receiving means 6 orthogonally detects the reflected wave signal received from the ultrasonic probe 3 to take out effective signals. Heart wall displacement detecting means 7 analyzes the orthogonally detected signals to obtain the instantaneous velocities of points in the region of interest ROI set on beam positions on a section of the heart wall, and integrates the velocities to trace the displacement motion of each point due to the heart beat. Integrated backscattering intensity detecting means 8 calculates the average power of the backscatter waves from the different points in displacement motion to obtain the integrated backscattering intensity IB. Variable frequency detecting means 9 measures out the variation frequency or variable cycle of the integrated backscattering intensity IB from the different points in the region of interest, and makes it available as information representing the local tissue characteristics of each point. Display output processing means 10 converts the variation frequency or variable cycle of the integrated backscattering intensity IB of each point into a suitable display form and displays in on the screen of the monitor 11. For instance, the magnitude of the variation frequency is converted into a suitable color (hue/saturation) matched with it in advance, and differences in or the extents of tissue characteristics in the region of interest can be made more readily perceivable by displaying the color in a patch form in the pertinent position in the M-mode image.

Figure 2:
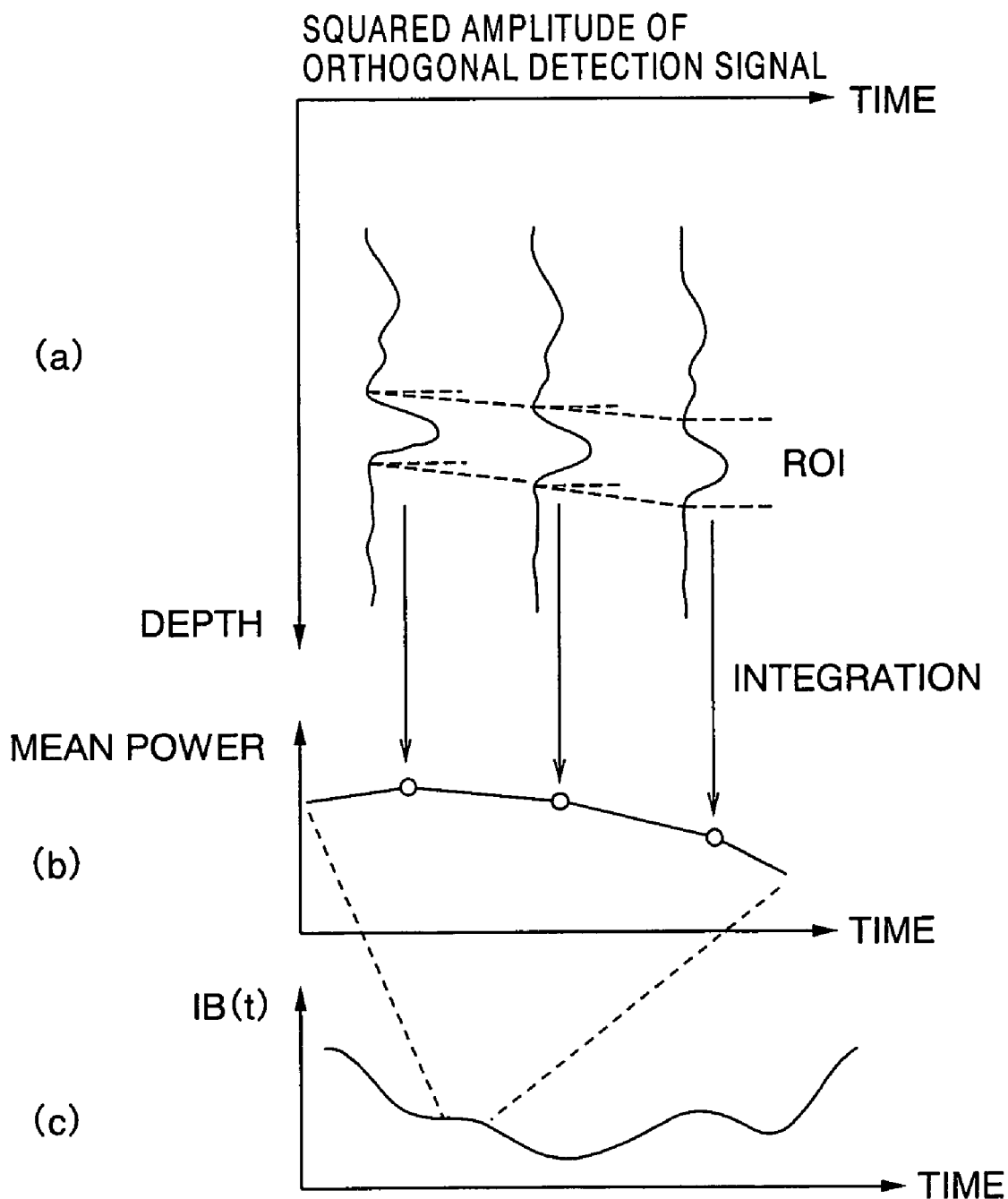
FIG. 2 illustrates the principle of calculating IB from the heart wall.

FIG. 2 illustrates the principle of calculating (or measuring; the same applies hereinafter) IB from the heart wall. In part (a) of FIG. 2, the horizontal axis represents the time, the vertical axis the depth, and the waveforms of signals resulting from amplitude squaring of the orthogonally detected signals of three reflected wave signals received respectively matching three consecutively transmitted ultrasonic pulses are shown side by side. Signal portions from the region of interest ROI are segmented by dotted lines. The part (b) of FIG. 2 shows the average power measured by integrated the signal portions segmented by the dotted lines, namely the integrated backscattering intensity IB. The part (c) of FIG. 2C shows an IB (t) waveform showing collectively in a time series the average power of the ROI signal portions measured similarly with respect to the reflected wave signals obtained from the transmission of other consecutive ultrasonic pulses.

The present invention provides the following effects.

(1) Since it is possible by the phased tracking method (Japanese Patent Application Laid-Open No. 2000-229078) to trace variations of the same position (depth from the ultrasonic probe) of the cardiac muscle within a beat, the region of interest can be set always regarding the same region of cardiac muscle (the region of interest automatically expands in the systole and automatically contracts in the diastole). For this reason, only variations in backscattering intensity can be measured without being affected by density variations within the region of interest. Measurement of variations in backscattering intensity within the region of interest, by reason of the physiology of the cardiac muscle, matches kymographic measurement of structural changes of muscle or the like. When the contracting/expanding function of the local cardiac muscle is damaged by a heart disease, the structural changes of muscle will decrease, and so will variations in backscattering intensity. There is no other way of bloodless inspection which can measure variations in the cardiac muscle structure during the systole and the diastole.

(2) The vibration of the heart wall can be measured even to high frequency components. Thus, it is made possible to trace the displacement of the same region of interest with high precision, and the scatter wave from the region of interest with a high time-resolution. By detecting the time cycle of its IB signal, the velocity of instantaneous thickness variation can be made assessable for each region of the local cardiac muscle.

Conventionally, the measurement of the backscatter wave from the same region of interest is performed at long intervals of time, tens of ms (msec) or even longer. By contrast according to the invention, the backscatter wave can be measured at short intervals of time (a high frequency of repetition) of hundreds of µs (µsec).

The variation cycle of the IB signal at short intervals of time is correlated to the velocity of local thickness variation of the heart wall due to the extension and contraction of the cardiac muscle. Therefore, by detecting the variation cycle of the IB signal from each of a plurality of regions of interest set in the cardiac muscle and superposing the motions of the heart on an M-mode image, it is made possible to evaluate the velocity of instantaneous thickness variation of each region of the local cardiac muscle.

(3) When the region of interest is set on one point, the IB signal enables the velocity of thickness variation around that one point from the reflected wave amplitude at that one point. This can be considered a very important contribution to enabling the velocity of thickness variation to be calculated. For instance, an arterial wall is also surrounded by unstriped muscles, and its inner diameter varies with a blood pressure variation within a beat, accompanied by a variation in wall thickness at the same time. It is made possible to measure variations in unstriped muscle structure, thereby making possible diagnosis of pathological variations in unstriped muscles and wall tissue structure.

The present invention will be described in detail below with reference to a mode of implementation thereof.

(1) IB Measurement Test on Human in Vivo (1.1) IB Measuring System

Figure 3:
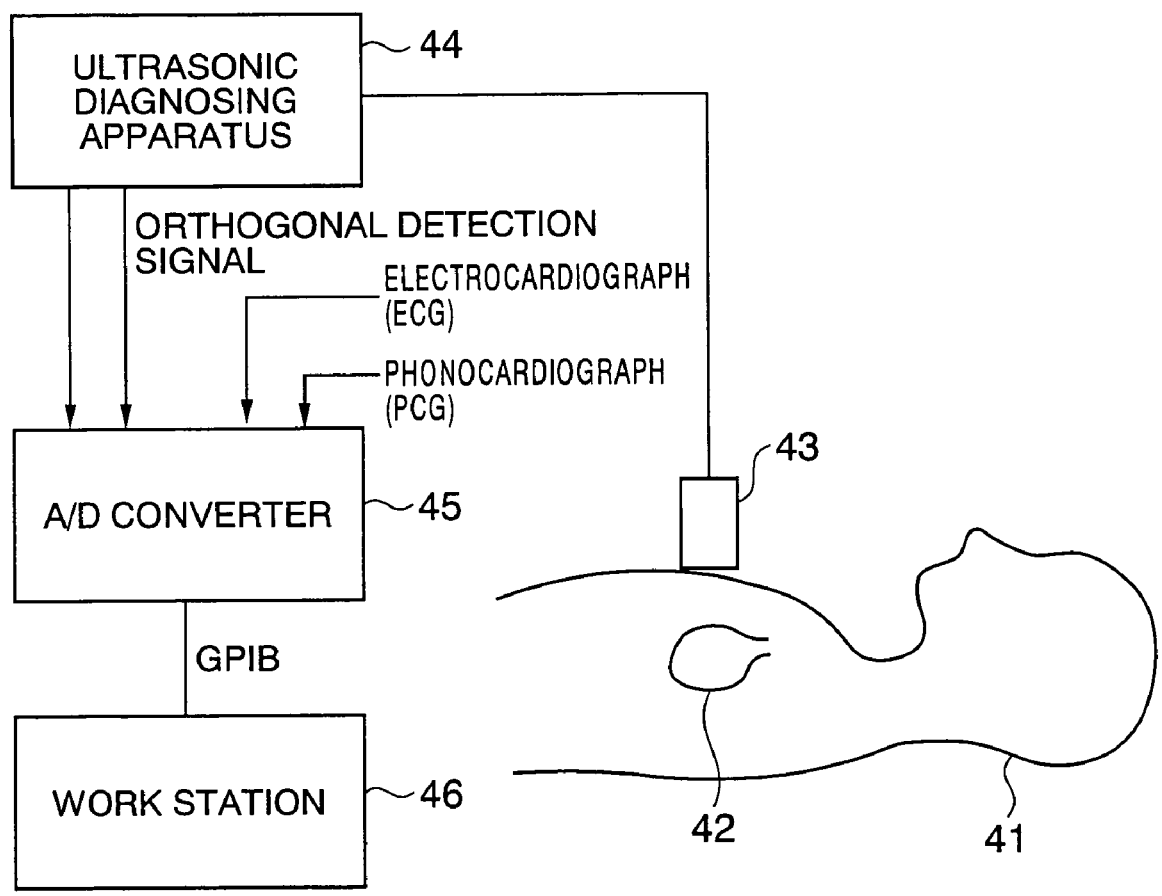
FIG. 3 schematically shows an IB measuring system used in a measuring test for demonstrating the invention.

FIG. 3 schematically shows an IB measuring system used in a measuring test for demonstrating the invention. In FIG. 3, reference numeral 41 denotes a subject, 42 a heart, 43 an ultrasonic probe, 44 an ultrasonic diagnosing apparatus, 45 an A/D converter, and 46 a work station. The ultrasonic diagnosing apparatus 44 can be one of any appropriate conventional type, and the analysis of reflected wave signals based on the invention is processed by a program built into the work station 46. As the ultrasonic diagnosing apparatus 44, Toshiba's SSH-140A (of 3.75 MHz in center frequency) was used. The ultrasonic diagnosing apparatus 44 percutaneously transmits and receives ultrasonics between the ultrasonic probe 43 and the heart wall at a repeated transmission frequency of 4.5 kHz, orthogonally detects the reflected wave signal which is received, and inputs it into the A/D converter 45. Electrocardiograph (ECG) and phonocardiograph (PCG) signals are also input into the A/D converter 45. The A/D converter 45 converts the orthogonally detected signal that has been input, and ECG and PCG signals from analog to digital at a sampling frequency of 10 MHz, and inputs the converted signals into the work station 46 via a GPIB interface to record them. The work station 46 measures the variation frequency of the backscattering intensity of the orthogonally detected signal that has been recorded by the analytical processing described with reference to FIG. 1, and supplies it for displaying on a screen together with a B-mode image, M-mode image, ECG and PCG. Actual examples of measurement will be described below with reference to FIG. 4 through FIG. 15.

(1.2) Result of IB Measurement Test on Human in Vivo

A healthy man was subjected to in vivo measurement of IB from his heart wall.

Figure 4:
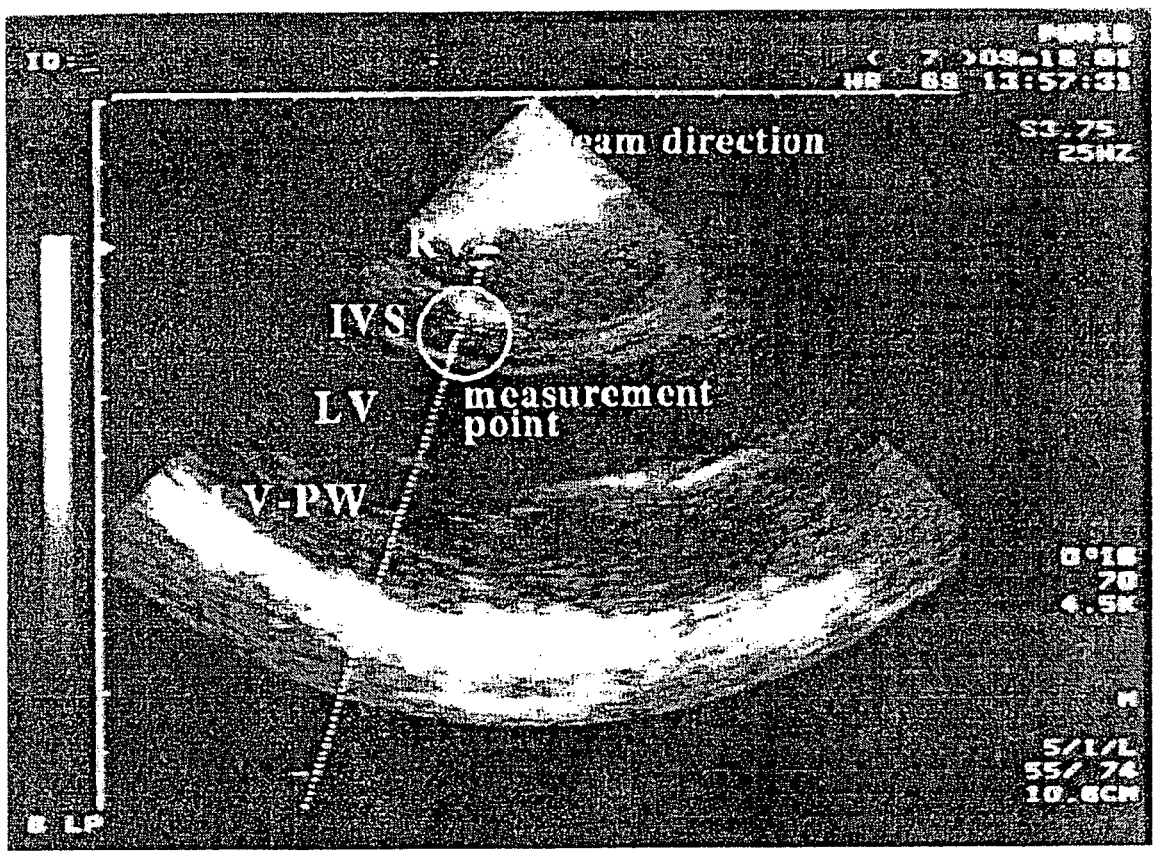
FIG. 4 shows a B-mode tomogram along the longer axis of the left ventricle of a subject 1 (24 years old, male).
Figure 5:
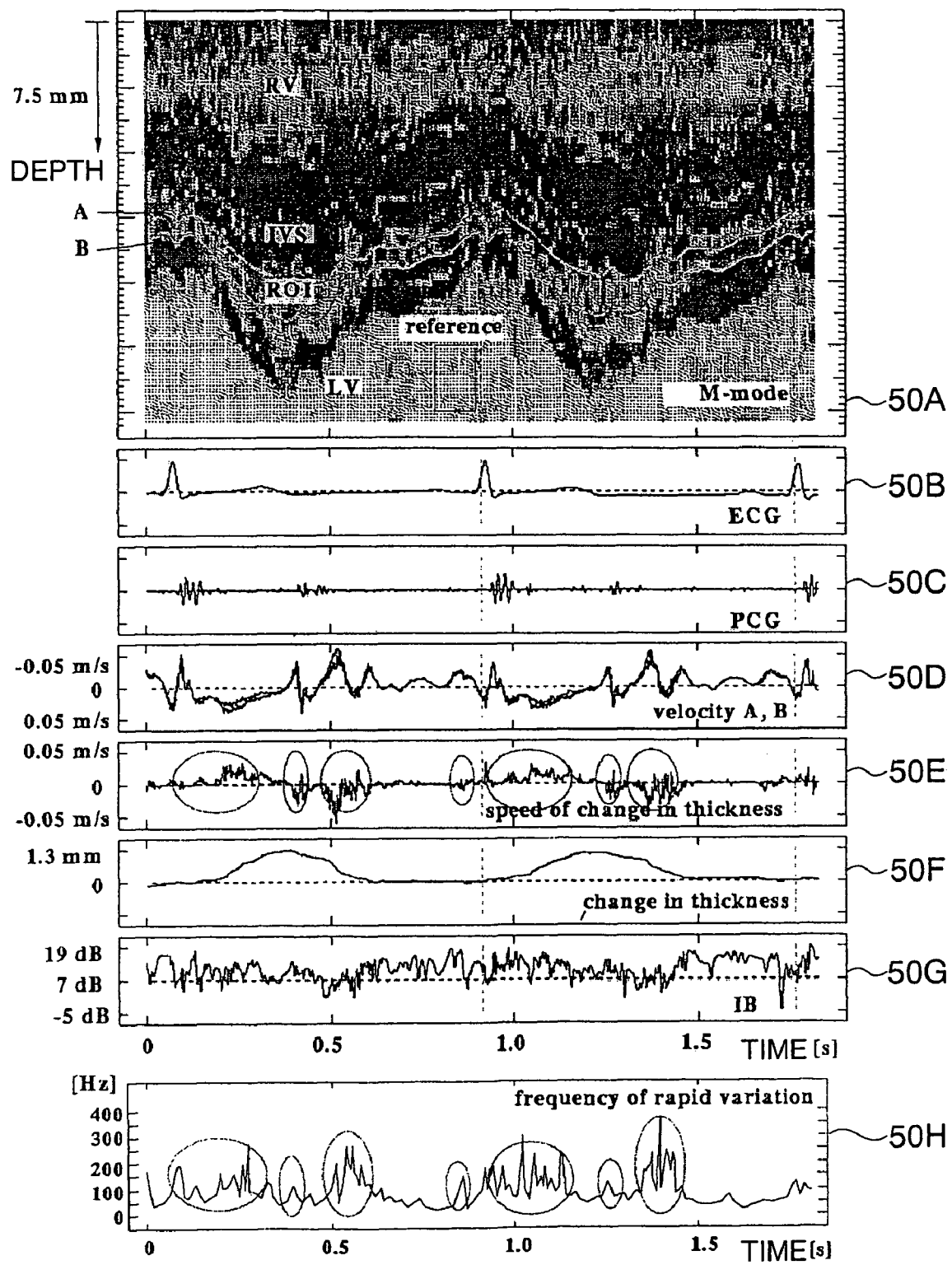
FIG. 5 is an ($\alpha$) waveform diagram showing the result of IB measurement from the interventricular septum in the beam direction.

FIG. 4 shows a B-mode tomogram along the longer axis of the left ventricle of the subject 1 (24 years old, male), and FIG. 5 shows the result of IB measurement from the interventricular septum in the illustrated beam direction in FIG. 5. An ROI of 1.2 mm is set in the interventricular septum of the subject 1 at the time of the R wave of ECG to obtain the IB value. As the position and thickness of the heart wall vary with the pulsation, the position and thickness of the ROI at each point of time is varied by using the result of tracking of both ends (points A and B) of the set ROI. Of the graphs of FIG. 5, 50A shows an M-mode image reconstructed from orthogonally detected signals and the result of tracking of points A and B superimposed over it, 50B an ECG, 50C a PCG, 50D velocity waveforms of points A and B superimposed over each other, 50E the velocity waveform of thickness variations between points A and B, 50F thickness variations between points A and B, 50G the IB signal, and 50H a variation frequency read from the waveform of the IB signal. The IB value from the heart wall is calibrated by using the IB value from blood calculated with the reference region in the lumen of the left ventricle shown in graph 50A being selected as the region of interest. From graph 50F, it is seen that the IB signal has, in addition to the already known CV synchronized having one heart beat as one cycle, a component varying at a high frequency superimposed over the CV. Further, this high frequency variable component varies at substantially the same frequency in the same phase during a beat, both in the first and second beats, and it can be qualitatively confirmed that the short cycle variable component of the IB signal is reproducible.

From graph 50H, it is seen that the IB signal varies at frequencies of about 50 to 200 Hz in the early to middle phases of contraction, about 50 to 100 Hz in the late phase of contraction, about 100 to 300 Hz in the early phases of expansion, and about 20 to 50 Hz in the middle to late phase of expansion. It is further seen from graphs 50E and 50H that the varying frequency of the IB signal rises in time phases where the velocity of thickness variation is great.

Figure 6:
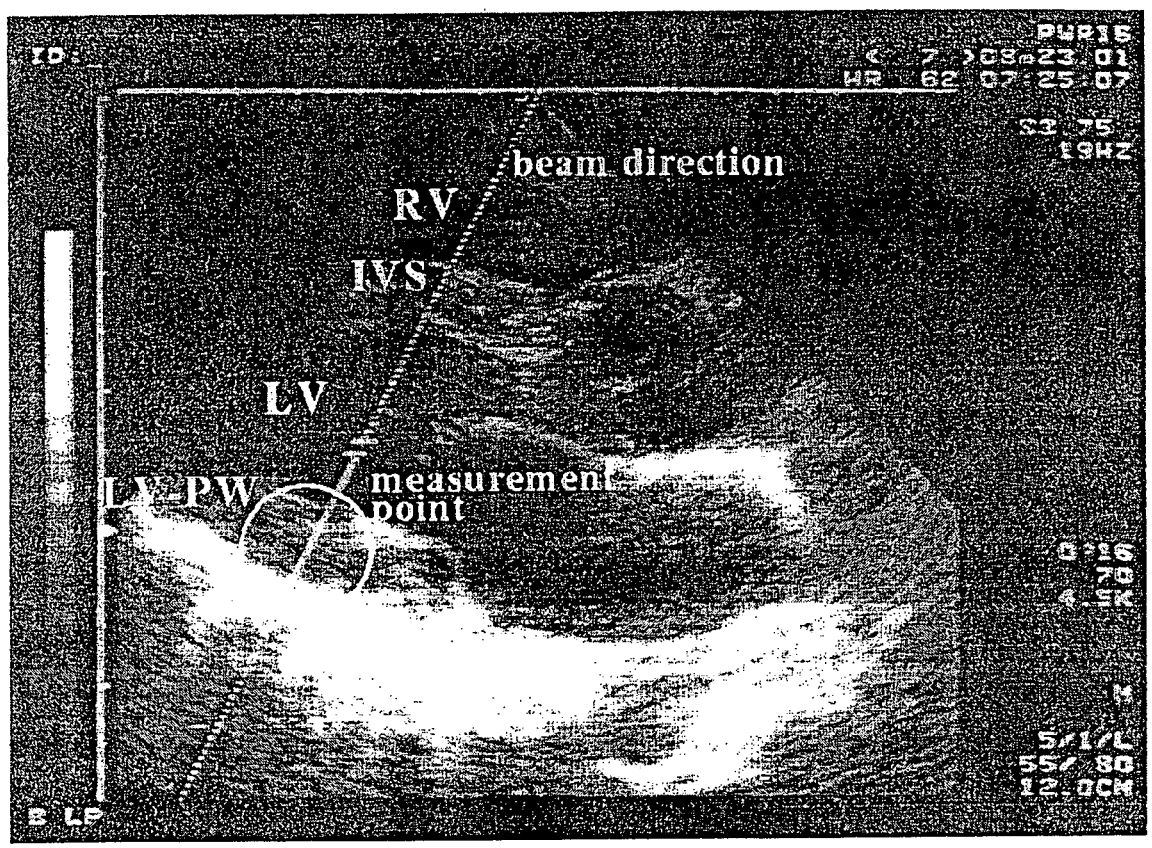
FIG. 6 shows a B-mode tomogram along the shorter axis of the left ventricle of a subject 2 (23 years old, male).
Figure 7:
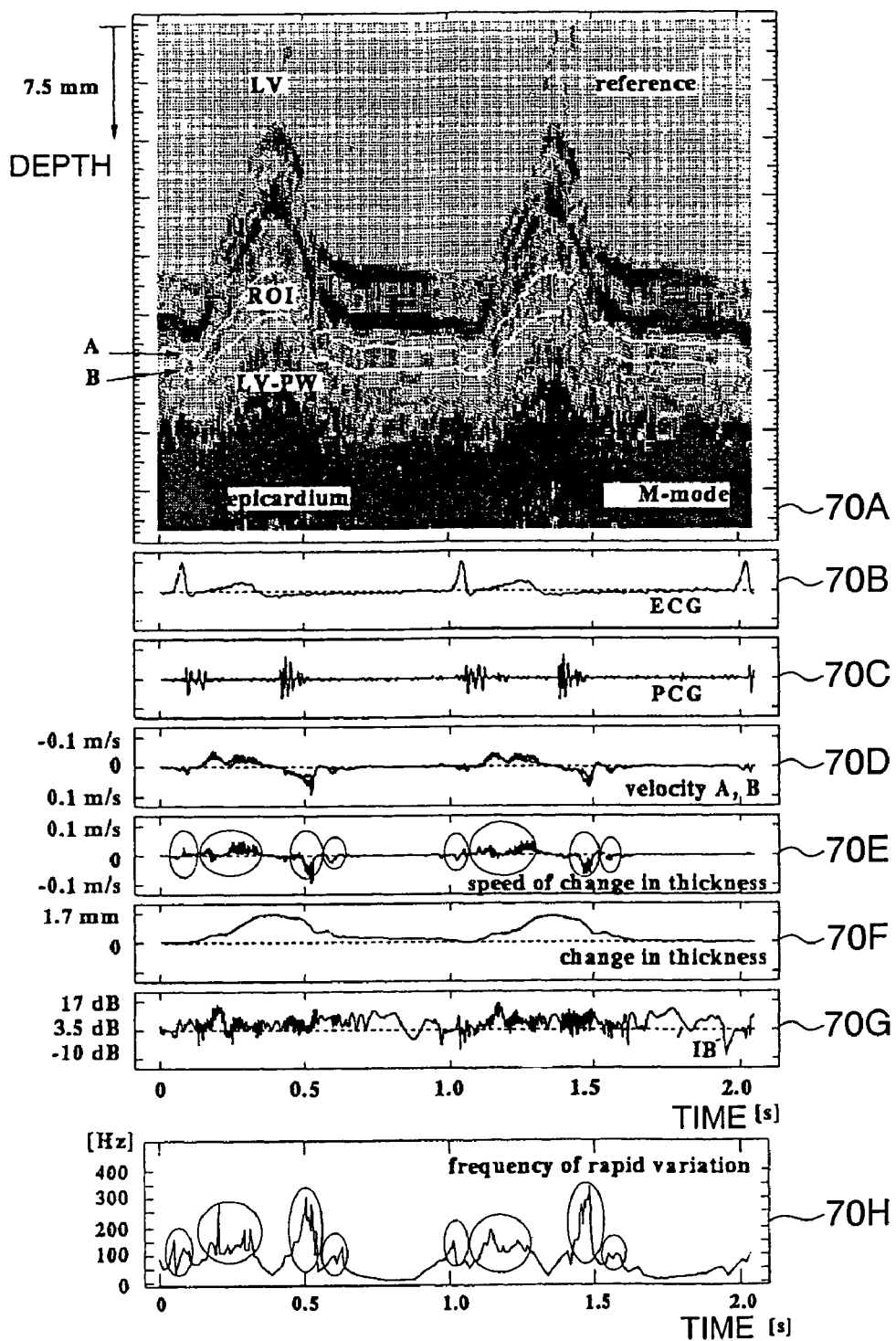
FIG. 7 is a waveform diagram showing the result of IB measurement from the free wall of the left ventricle in the beam direction.

FIG. 6 shows a B-mode tomogram along the shorter axis of the left ventricle of a subject 2 (23 years old, male), and FIG. 7 shows the result of IB measurement from the free wall of the left ventricle in the illustrated beam direction in FIG. 7. The graphs of FIG. 7 match their respective counterparts in FIG. 5. As is the case with the subject 1, an ROI of 1.2 mm is set in the free wall of the left ventricle at the time of the R wave of ECG to obtain the IB value at each point of time. It can be qualitatively confirmed from graph 70F that the IB signal from the free wall of the left ventricle is also reproducible between beats.

It is seen from graph 70H that the IB signal varies at frequencies of about 100 to 200 Hz in the early to middle phases of contraction, about 30 to 50 Hz in the late phase of contraction, about 100 to 300 Hz in the early to middle phases of expansion, and about 20 to 30 Hz in the late phase of expansion.

It has been revealed that, whether from the interventricular septum or from the free wall of the left ventricle, the IB signal varies at a frequency of tens of Hz to hundreds of Hz within one beat. Especially in the time phases in which the thickness of the heart wall significantly varies, such as the early to middle phases of contraction and the early phase of expansion, the IB signal varied at a higher frequency than in other time phases.

(1.3) Measurement of IB Signals From Different Layers of Heart Wall

Figure 8:
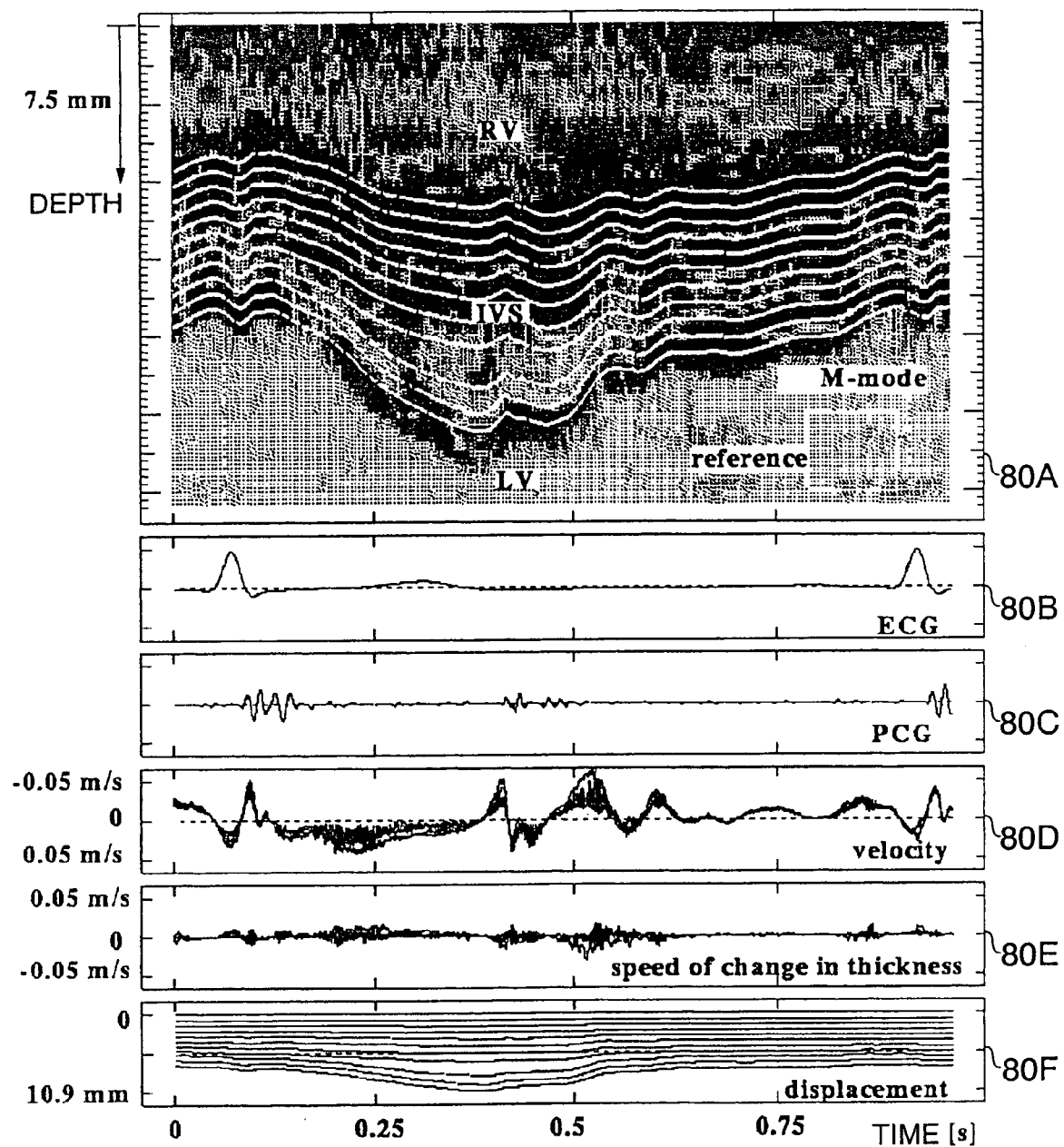
FIG. 8 is a waveform diagram showing the results of IB measurement from different layers of the interventricular septum.
Figure 9:
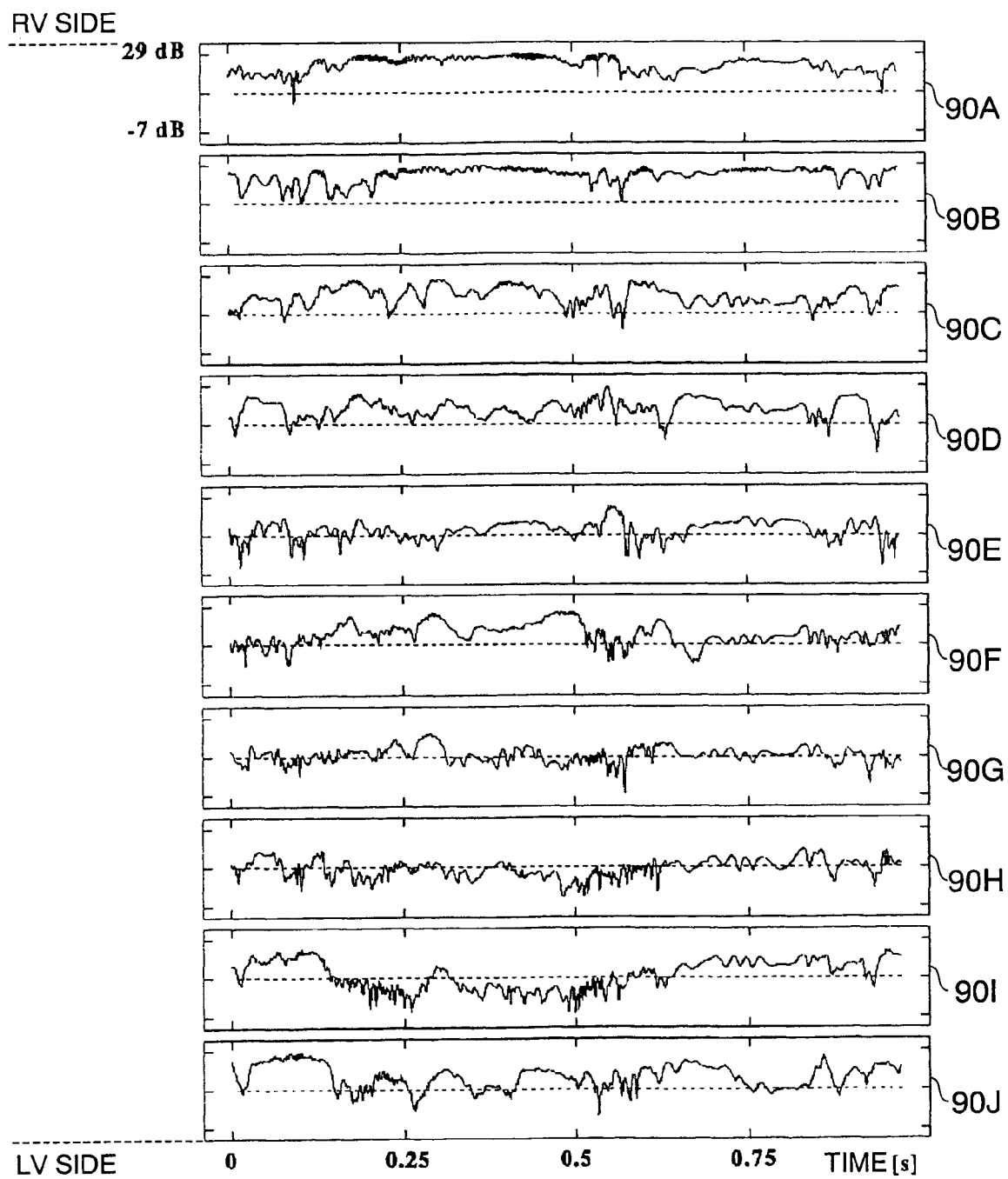
FIG. 9 is a waveform diagram of IB signals from different layers of the interventricular septum.
Figure 10:
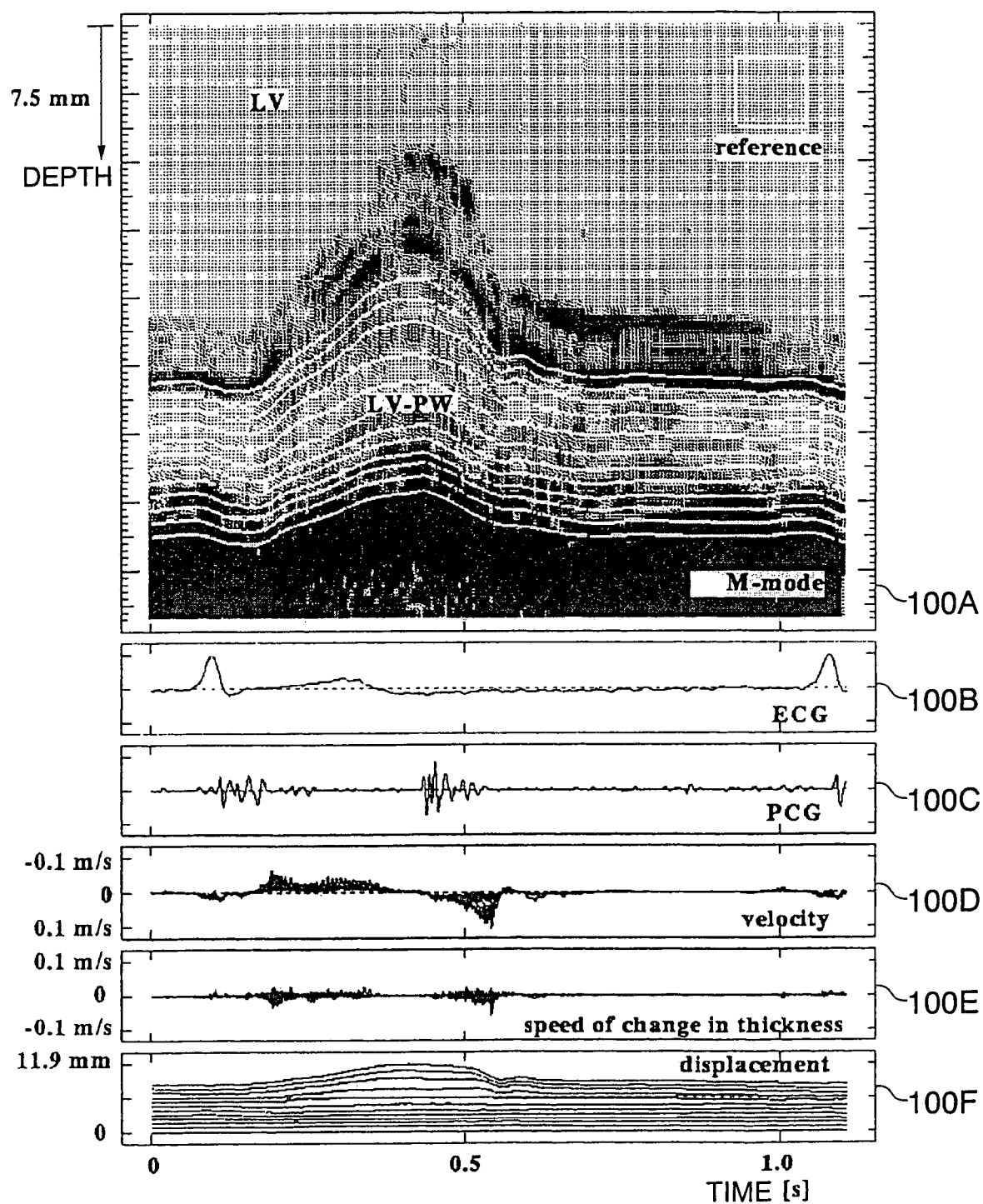
FIG. 10 is a waveform diagram showing the results of IB measurement from different layers of the free wall of the left ventricle in the beam direction.
Figure 11:
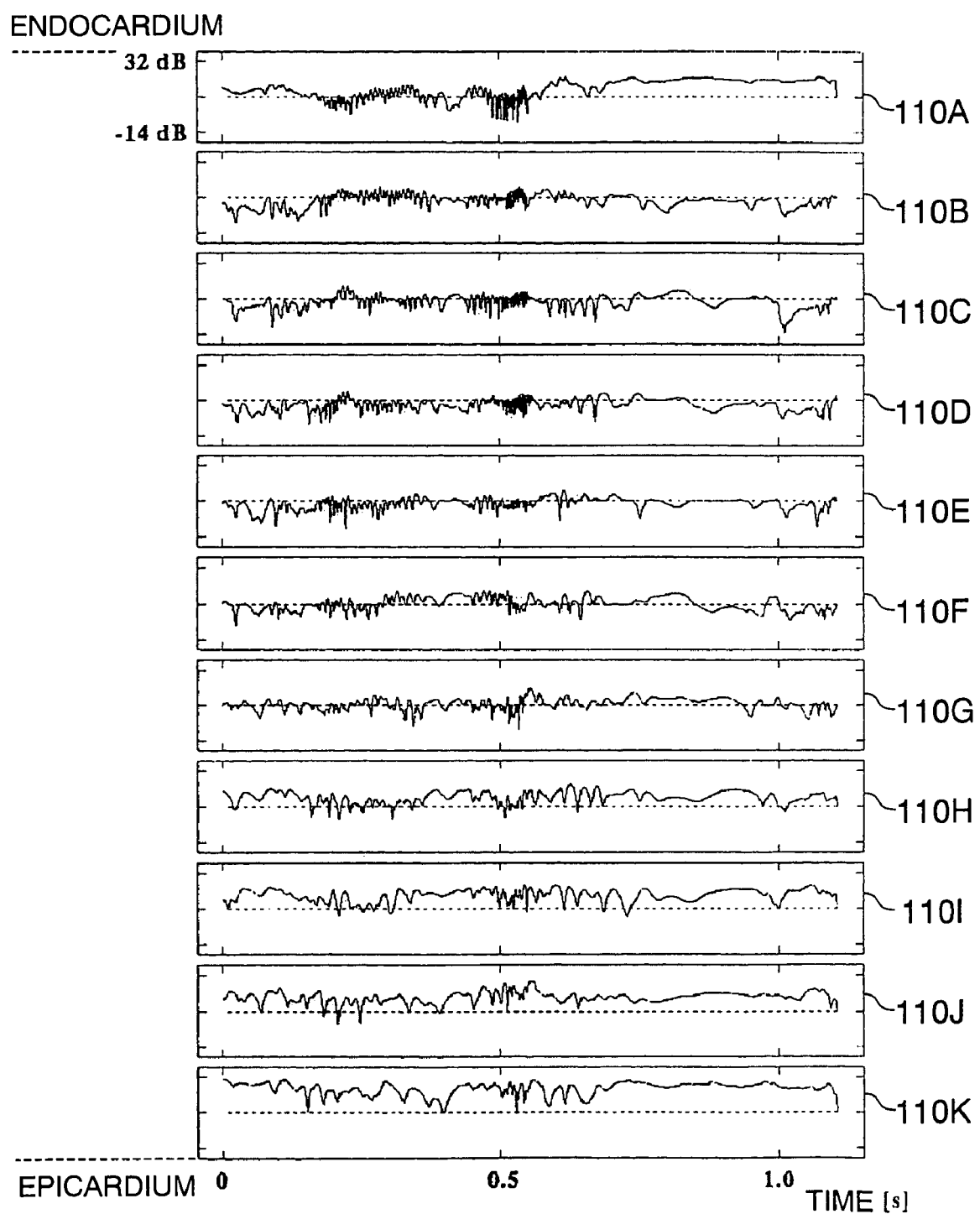
FIG. 11 is a waveform diagram of IB signals from different layers of the left ventricle.

Next, the heart wall was divided into a plurality of layers, and the IB signal from each layer of the heart wall, each layer being set as the region of interest. For the data shown in FIG. 5 and FIG. 7, 10 layers of region of interest are set in the interventricular septum, and 11 layers in the free wall of the left ventricle, in a thickness of 750 µm per layer at the timing of R wave of electrocardiogram, and the IB from each layer is calculated. FIG. 8 and FIG. 9 show the results of IB measurement from different layers of the interventricular septum, and FIG. 10 and FIG. 11 show those from different layers of the free wall of the left ventricle. In FIG. 8, graphs 80A through 80E respectively match graphs 50A through 50E in FIG. 5, and graph 80F shows variations of the position (thickness) of each layer (the same is true in FIG. 10). In FIG. 9, graphs 90A through 90J show the results of IB calculation from the 1st through 10th layers, respectively. In FIG. 11, graphs 110A through 110K show the results of IB calculation from the 1st through 11th layers, respectively.

The variation frequency of the IB signal was found rising from the inner tunic side of the right ventricle toward the inner tunic side of the left ventricle in the interventricular septum and from the epicardium side toward the middle tunic side of the left ventricle in the free wall of the left ventricle.

(1.4) Relationship Between Short Cycle Variation Frequency of IB Signal and Local Thickness Variation of Heart Wall The short cycle variation frequency of the IB signal was found tending to be higher in time phases where the velocity of thickness variation of the region of interest was higher. Following is a consideration on the relationship between the short cycle variation frequency of the IB signal and the velocity of the local thickness variation of the heart wall. The velocity $S_i(t)[(m/s)/m]$ of the local thickness variation of the heart wall is represented by [Equation 2] below.

$$S_i(t) = \frac{v_i(t) - v_{i-1}(t)}{x_i(t) - x_{i-1}(t)} \quad \text{[Equation 2]}$$

Here, $V_{i-1}(t)$ and $V_i(t)$ are velocities at the i-1-th and i-th points respectively, and $X_{i-1}(t)$ and $x_i(t)$ are displacements at the i-1-th and i-th points respectively. The spatial difference $V_i(t)-V_{i-1}(t)$ of velocity represents the thickness variation of the i-th layer over time, and is normalized with the instantaneous thickness $X_i(t)-X_{i-1}(t)$ of the layer to obtain the thickness variation velocity of the layer. This thickness variation velocity is averaged over time during the variation cycle $\Delta T(t)$ of the IB signal, and the average $S_{ave}(t)[(m/s)/m]$ of the thickness variation velocity is calculated by [Equation 3] below.

$$S_{ave}(t) = \frac{1}{\Delta T(t)} \int_{t}^{t+\Delta T(t)} S_i(\tau) d\tau \quad \text{[Equation 3]}$$

Figure 12:
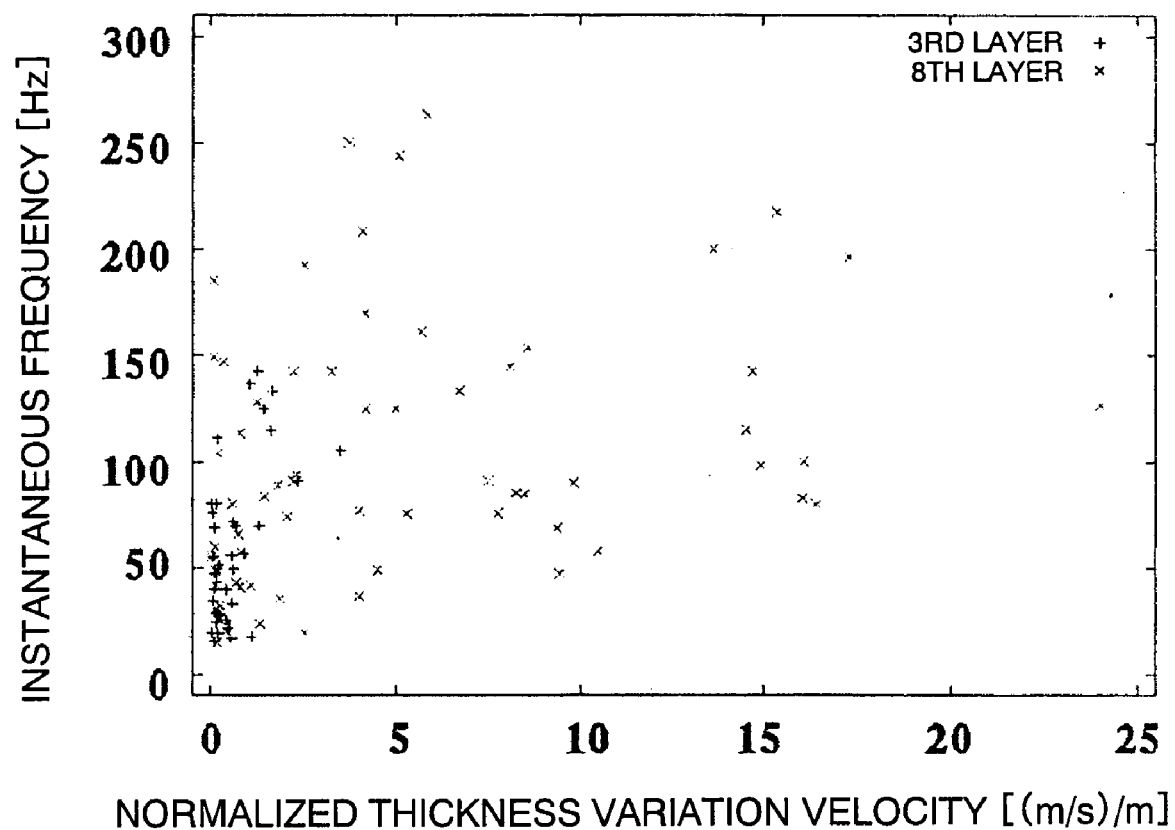
FIG. 12 is a graph showing the relationship between the variation frequency f(t) (=1/$\Delta$T(t)) of IB signals from the interventricular septum and the absolute value $S_{ave}(t)$ of the average of the thickness variation velocity in the region of interest.
Figure 13:
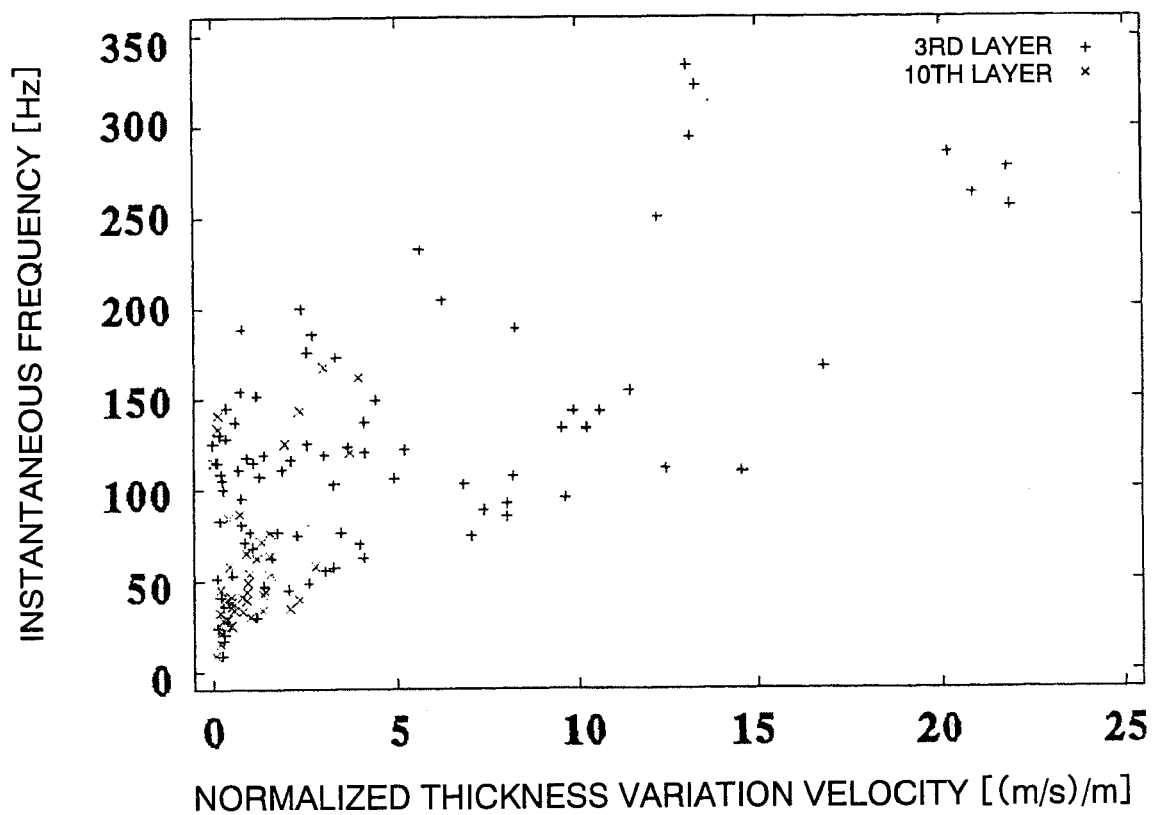
FIG. 13 is a graph showing the relationship between the variation frequency f(t) (=1/$\Delta$T(t)) of IB signals from the free wall of the left ventricle and the absolute value $S_{ave}(t)$ of the average of the thickness variation velocity in the region of interest.

FIG. 12 and FIG. 13 are graphs showing the relationship between the thickness variation velocity of the heart wall and the variation frequency of IB signals, i.e. the relationship between the variation frequency f(t) (=1/ΔT(t)), respectively from the interventricular septum and the free wall of the left ventricle, and the absolute value $S_{ave}(t)$ of the average of the thickness variation velocity of the region of interest. There is witnessed a trend for the variation frequency of the IB signal to become higher when the absolute value of the thickness variation velocity is greater, and in the free wall of the left ventricle in particular the thickness variation velocity and the frequency of the IB signal are found substantially proportional to each other.

(1.5) Illustration of Short Cycle Variation Frequency of IB Signal

From the results stated above, the variation frequency (=1/variation cycle) of the IB signal is found correlated to the thickness variation velocity. Hence, the variation frequency $f_{mean}$[Hz] of the IB signal is detected according to [Equation 4] below for each of the plurality of regions of interest set in the cardiac muscle.

$$f(t) = \frac{\int f \times |S(f,t)|^2 df}{\int |S(f,t)|^2 df} \quad \text{[Equation 4]}$$

Figure 14:
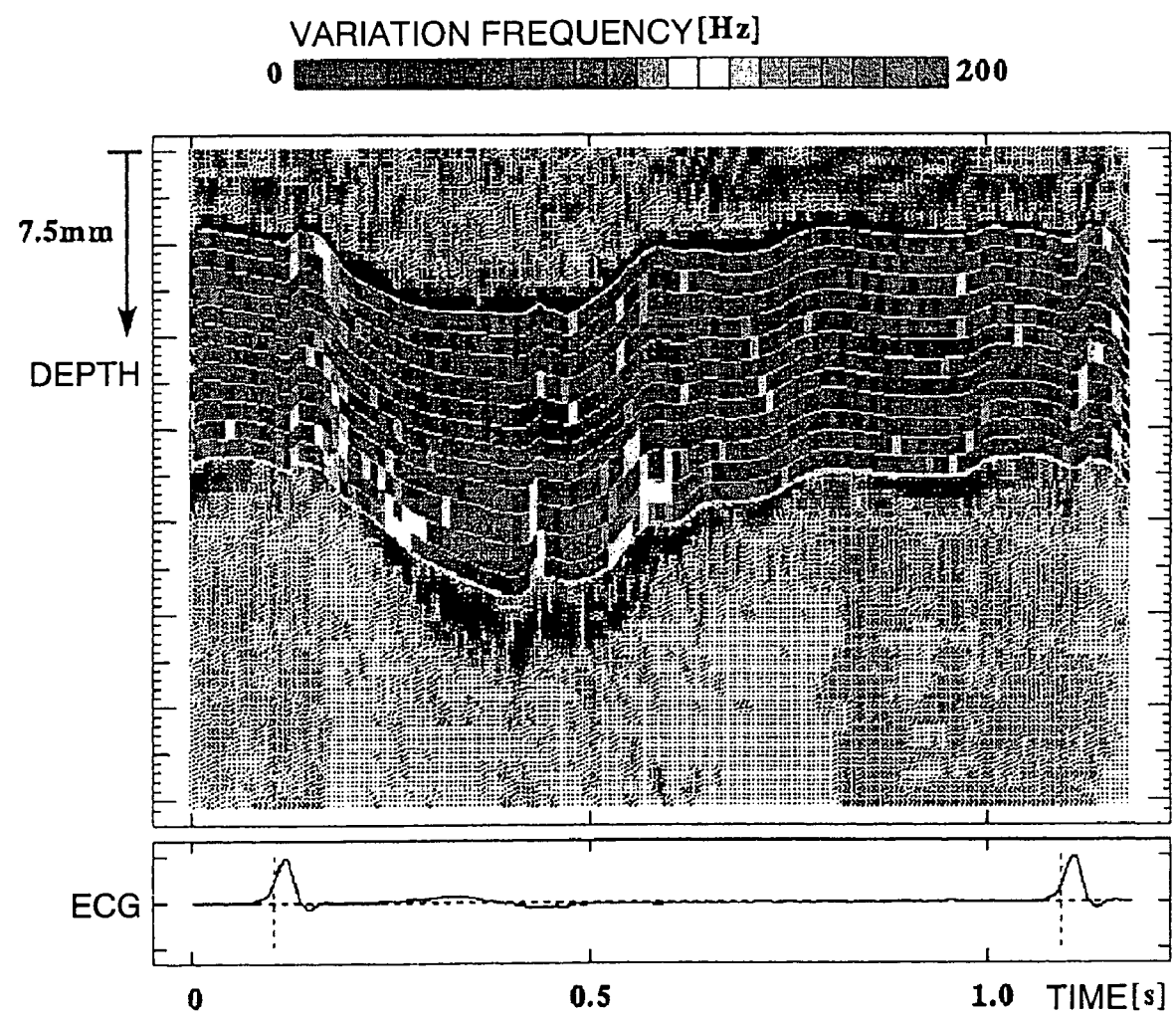
FIG. 14 is a diagram obtained by superposing the distribution of the center frequency of the variations of IB signals from the interventricular septum on the M-mode image of the heart motion.
Figure 15:
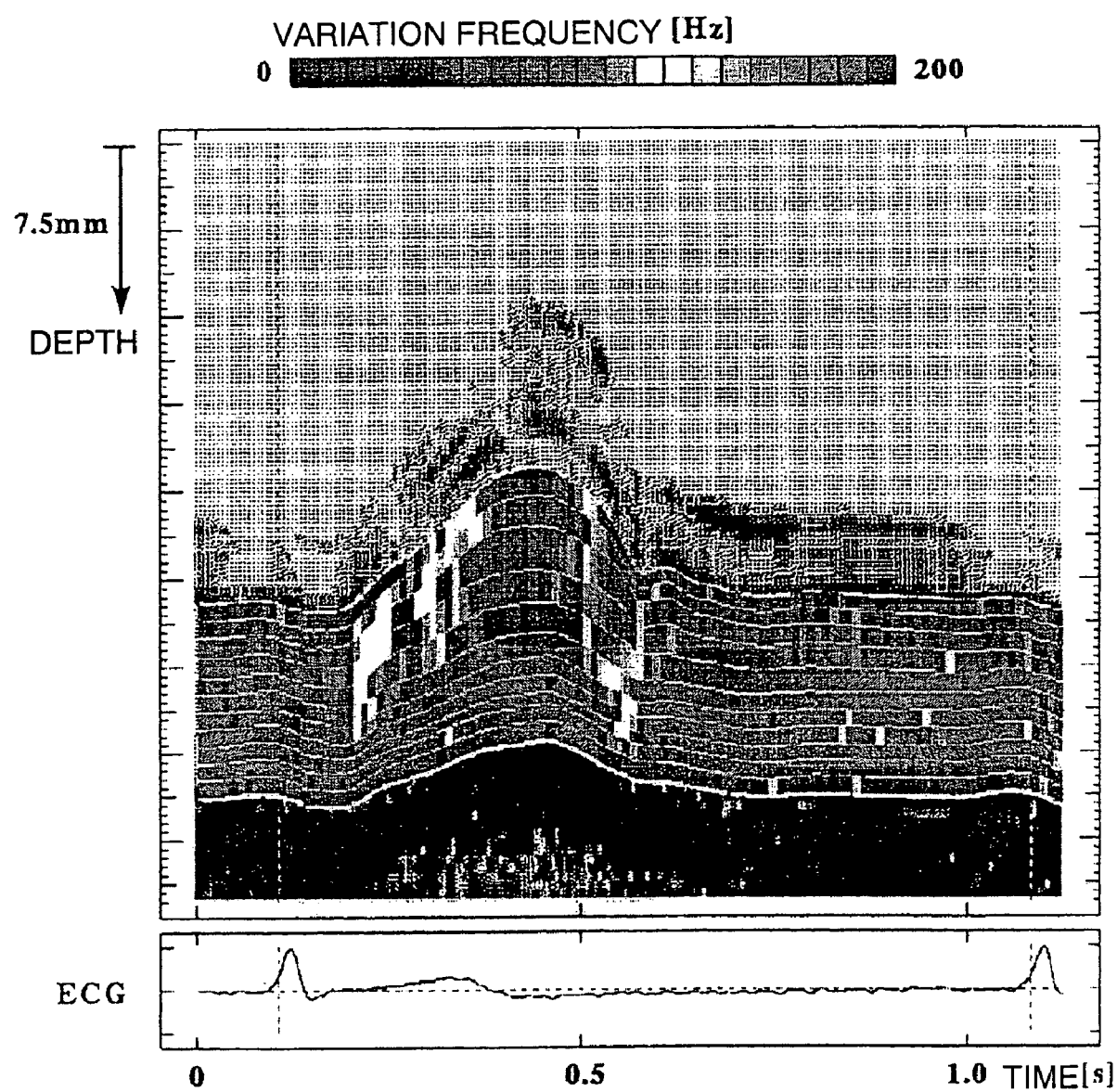
FIG. 15 is a diagram obtained by superposing the distribution of the center frequency of the variations of IB signals from the free wall of the left ventricle on the M-mode image of the heart motion.

Here, S(f, t) is a power spectrum obtained by the Fast Fourier Transform on the IB signal. By superposing the variation frequency $f_{mean}$ of the IB signal thereby obtained over the M-mode image of heart motion, FIG. 14 or FIG. 15 is obtained. Certainly, high frequency components are found in phases where the thickness variation is greater, and it is seen that the instantaneous thickness variation velocity can be evaluated for each region of local cardiac muscle according to the variation frequency of the IB signal.

(2) Consideration of IB Measurement Test (2.1) Cause for Short Cycle Variation of IB Cells of cardiac muscle are mutually propped by supports comprising collagen fibers, which are bundled into cardiac muscle fiber fascicles, which are further wrapped in a collagen fiber tissue. The scattering of ultrasonics within the heart wall is attributed to mismatching in acoustic impedance between the cells of cardiac muscle and the interstitial tissue mainly comprising collagen fibers.

The cardiac cycle variations of IB were attributed to changes in the orientation or volume density of the interstitial tissue, which is a scatterer, or in the acoustic impedance of cardiac muscle cells along with the extension and contraction of the cardiac muscle. However, variations in the orientation or volume density of the interstitial tissue are due the extension and contraction of the cardiac muscle, and their cycle is equal to the pulsation of the heart. They can explain the variations of IB in one cycle per beat, but not the variations of a few tens to a few hundreds of Hz, which have been witnessed this time.

We consider the short cycle variations of IB to be due to interference between scattering waves within the heart wall. As the thickness of the heart wall varies with the extension and contraction of the cardiac muscle and the spaces between scatterers in the wall vary, and the interference between scattering waves from different scatterers presumably gives rise to intensity variations of the backscatter wave. Considered in this way, the greater the variation of spaces between scatterers, the shorter the cycle of intensity of interfering scattering waves is likely to be. This is in agreement with the experimental finding that the variation frequency of the IB signal is higher in phases wherein the thickness of the heart wall vary more greatly, such as the early phase of contraction or expansion, than in other phases.

(2.2) Intramural Variation of Variation Frequency of IB Signal

As shown in FIG. 12 and FIG. 13, the variation frequency of the IB signal differs from layer to layer in the heart wall. The variation frequency was found to rise from the right ventricle toward the left ventricle in the interventricular septum, while it rose from the outer tunic side toward the endocardium in the free wall of the left ventricle.

The cardiac muscle does not run uniformly within the heart wall. In the free wall of the left ventricle, in a short axis section of the left ventricle, it runs at an angle of about −70° relative to the direction of the circumference of a circle on the outer tunic side and at about 60° in the inner tunic side, and the running of the cardiac muscle between them consecutively varies. This is regarded as suggesting the unevenness of the structure of the heart wall contributing to the scattering of ultrasonics within the heart wall.

The contracting function of the cardiac muscle is known to be higher on the inner tunic side of the left ventricle than on the inner tunic side of the right ventricle and the epicardium side. Myers et al., in a canine experimental model, embedded threads in the heart wall, observed the outcome in the M-mode, and found that, where a thread embedded at the center of the wall, the role of the endocardium side was greater with an 87% contribution to the wall thickness increase (Circulation 74, 164-172, 1986). This finding is in agreement with the calculated thickness variations of the heart wall shown in 80F of FIG. 8 and 100F of FIG. 10.

The intramural variations of the variation frequency of the IB signal seems to reflect such uneven running of the cardiac muscle and the difference in contracting function.

(3) Embodying System

Figure 16:
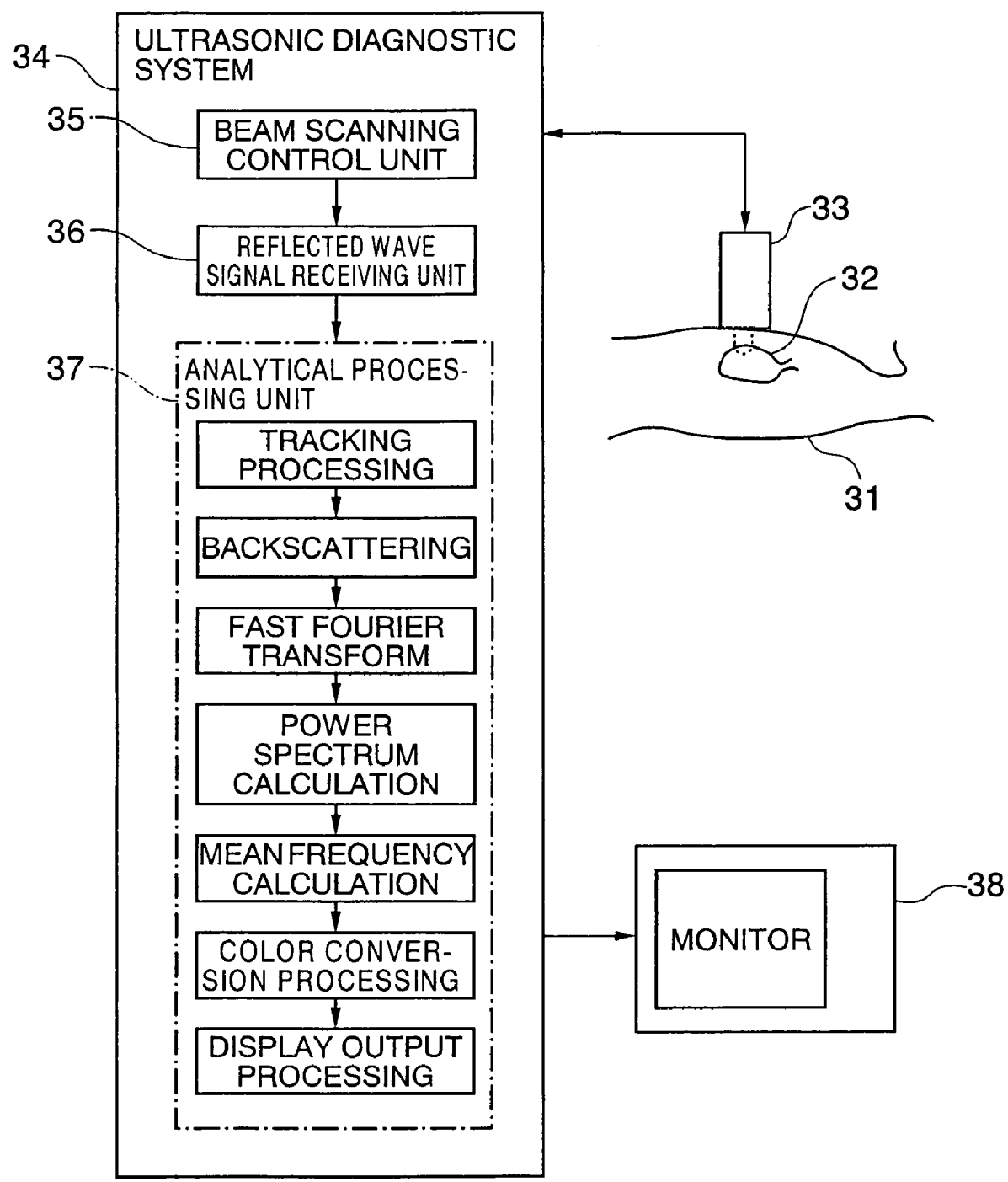
FIG. 16 shows a structure of one preferred embodiment of the invention, which is an ultrasonic diagnostic system.
Figure 17:
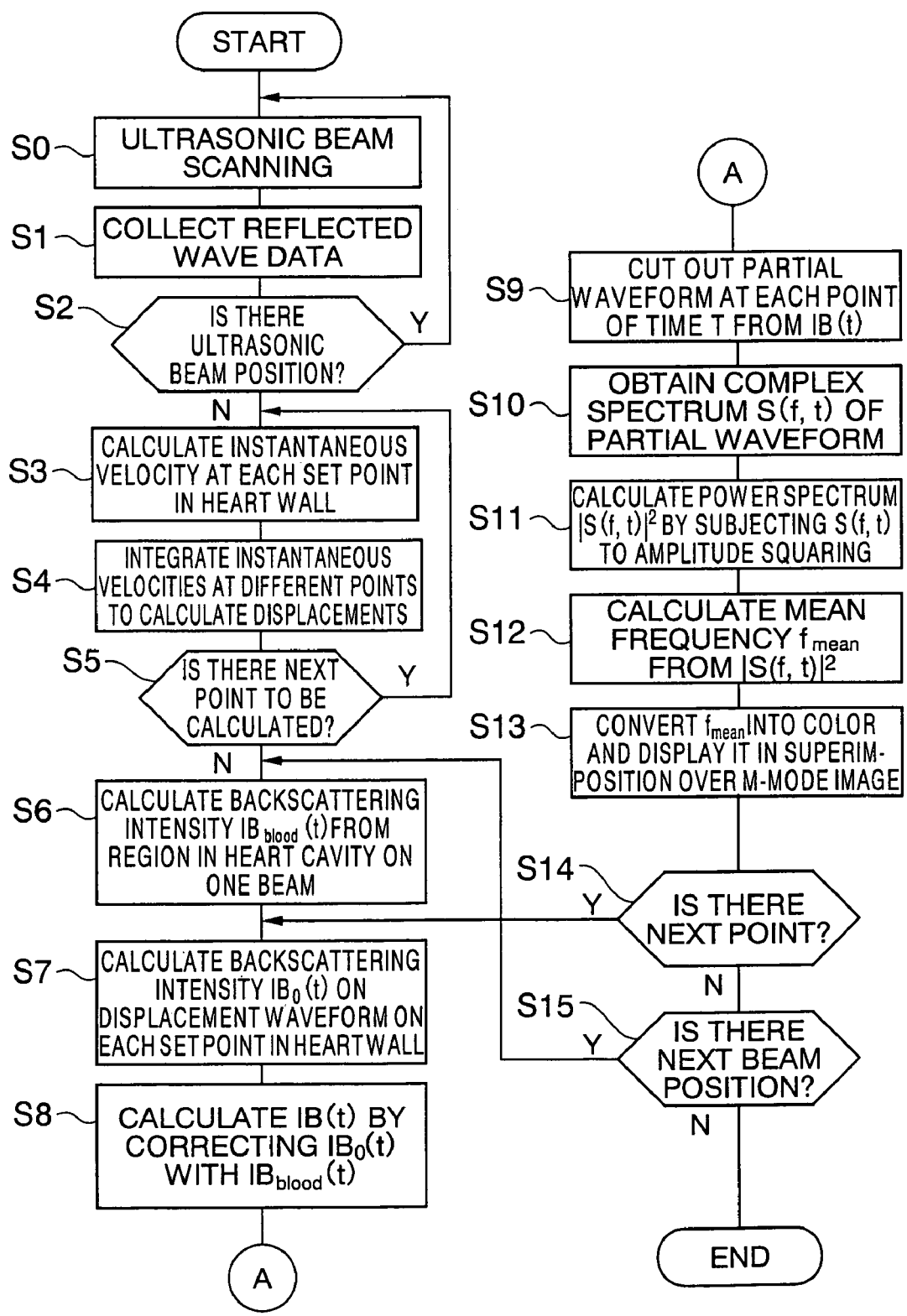
FIG. 17 shows an overall flow chart of ultrasonic diagnosis processing by an embodiment of the invention.
Figure 18:
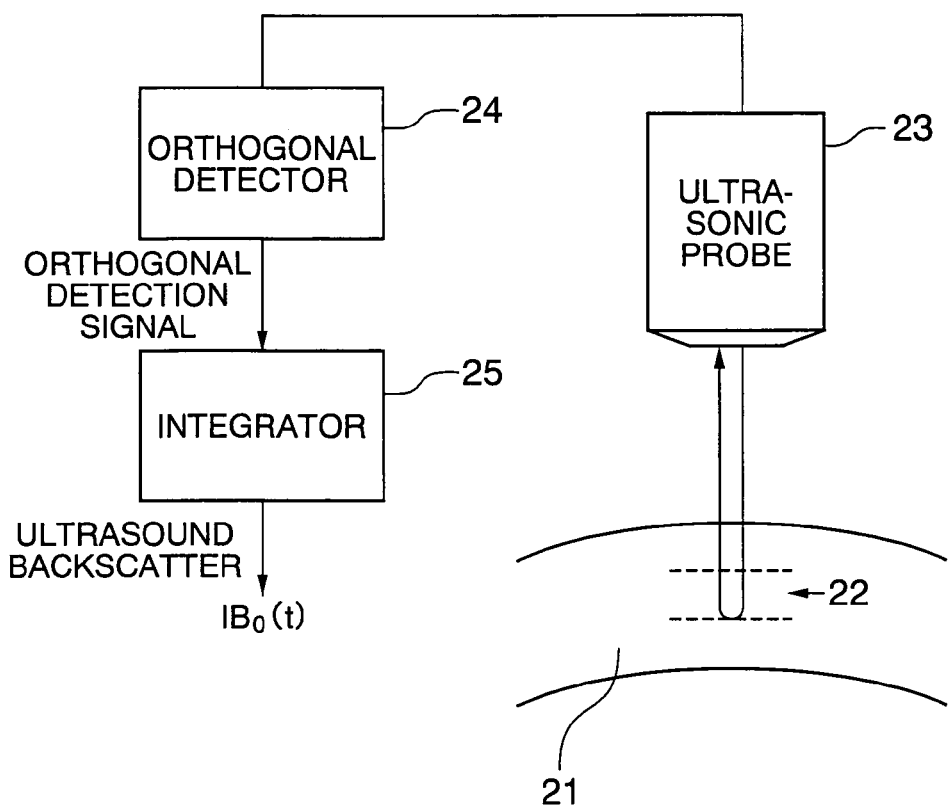
FIG. 18 is a diagram outlining an IB measuring system.
Figure 19:
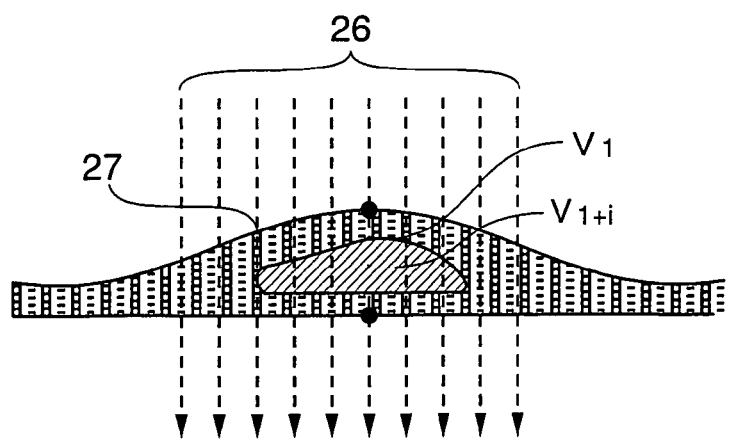
FIG. 19 shows an image of elasticity modulus distribution of an atheroma on a carotid wall, outlining the IB measuring system which measures out the thickness variation $\Delta$h(t) of the layer held between measurement points (i) and (i+1) in the arterial wall.

An ultrasonic diagnostic system embodying the present invention will now be described. FIG. 16 shows a structure of one preferred embodiment of the invention, which is the ultrasonic diagnostic system, and FIG. 17 shows an overall flow chart of ultrasonic diagnosis processing by the system.

In FIG. 16, reference numeral 31 denotes a subject, 32 a heart, 33 an ultrasonic probe, 34 an ultrasonic diagnostic system, 35 a beam scanning control unit, 36 a reflected wave signal receiving unit, 37 an analytical processing unit, and 38 a monitor.

The beam scanning control unit 35 controls the scanning position of an ultrasonic beam radiated from the ultrasonic probe 33 and the transmission of an ultrasonic pulse. The reflected wave signal receiving unit 36 receives and orthogonally detects a reflected wave synchronized with the transmission of the ultrasonic pulse. The analytical processing unit 37 is inputted the orthogonally detected signal, detects the displacement of the region of interest accompanying the pulsation of the heart by tracking, and calculates the integrated backscattering intensity $IB_o(t)$ by measuring the backscatter wave in the position of that displaced region of interest. In this analysis, an IB value $IB_{blood}$ based on a scattered wave from the blood in the ventricular lumen behind the heart wall is measured, with reference to which the IB signal $IB_o(t)$ from the heart wall is corrected to generate IB(t). A partial waveform is cut out of this IB (t) at each point of time by using a suitable window function, and subjected to fast Fourier transform to obtain a spectrum, whose amplitude is squared to obtain a power spectrum. Then the position of the center of gravity of the power spectrum is determined to calculate the mean frequency, which is adopted as the variation frequency value of the backscattering intensity. The variation frequency value thereby obtained is converted into a color corresponding to its magnitude, superimposed over an M-mode image and subjected to other processing, and the result is displayed on the screen of the monitor 38.

Next will be described the operation in further detail with reference to successive steps S0 through S15 of the overall flow charted in FIG. 17.

S0: An ultrasonic pulse is transmitted for scanning one of the ultrasonic beam positions of a B-mode image.

S1: Reflected wave data are collected.

S2: When there is a next ultrasonic beam position, the process will return to S0 to repeat scanning.

S3: The instantaneous velocity at each set point in the heart wall on one ultrasonic beam is calculated on the basis of the reflected wave data (phased tracking method).

S4: The instantaneous velocities are subjected to time integral to calculate the displacements (phased tracking method).

S5: Steps from S3 onward are repeated until the displacement is calculated for every set point.

S6: The backscattering intensity from a region comprising only of blood in the heart cavity (IB signal $IB_{blood}(t)$) is calculated with respected to one beam position.

S7: The backscattering intensity on the displacement waveform on each set point (IB signal $IB_o(t)$) is calculated.

S8: The backscattering intensity from the heart wall ($IB_o(t)$) is corrected with $IB_{blood}(t)$ to calculate IB(t).

S9: IB(t) is cut out by applying the windowing function to the surroundings of each point of time t.

S10: The cut-out waveform is subjected to fast Fourier transform to obtain a complex spectrum S(f, t).

S11: The complex spectrum S(f, t) is subjected to amplitude squaring to obtain a power spectrum $|S(f, t)|^2$.

S12: The center of gravity of the power spectrum $|S(f, t)|^2$ is determined to obtain a mean frequency $f_{mean}$.

S13: The mean frequency $f_{mean}$ is converted into a suitable color, displayed by superimposing over the position of the matching set point in an M-mode image to obtain an estimated value of thickness variation (examples shown in FIG. 13 and FIG. 14).

S14: The processing to calculate the mean frequency $f_{mean}$ for every point on a beam and display it superimposed over the M-mode image is repeated from S7 onward.

S15: Upon completion of processing one beam, the process returns to S6, the processing is repeated for the next beam position and, when the superimposed display of the mean frequency $f_{mean}$ converted into a color over the M-mode has been accomplished for every ultrasonic beam position, the process is completed.

The present invention is to provide entirely new means of noninvasive diagnosis for tissue characterization of the cardiac muscle, which has been prohibitively difficult in clinical practice up to date. According to the invention, the health of a cardiac muscle can be judged from variations in IB measurement along with the structural changes of cardiac muscle fibers in the systole and the diastole, the occurrence of variations of the IB measurement over time in short cycles and the high velocity of thickness variations. On the other hand, any damage to the extending/contracting function of a cardiac muscle inflicted by myocardial infarction or the like can be judged from the absence of these characteristics which a healthy muscle would manifest, and accordingly more accurate diagnosis is made possible.

What is claimed is:

1. An ultrasonic diagnostic system for preparing a diagnostic data including image by transmitting ultrasonic pulses to a living tissue, and receiving and analyzing reflected waves of the ultrasonic pulses, the ultrasonic diagnostic system comprising:

a beam scanning means for transmitting an ultrasonic beam having a plurality of ultrasonic pulses to a living tissue while successively changing over the radiating position of said ultrasonic beam, said plurality of ultrasonic pulses being transmitted at a repeated transmission frequency of a few kHz, said living tissue being a heart wall;

a reflected wave receiving means for receiving a plurality of wave signals reflected at the heart wall;

an analytical processing means for calculating a displacement waveform of a region of interest (ROI) by applying a phased tracking method to the received plurality of wave signals, for changing a position and size of the region of interest (ROI) based on the calculated displacement waveform, for calculating the plurality of backscattering intensity signals during one pulsation of the heart and for measuring the plurality of backscattering intensity signals during one pulsation of a heart by using a scattering wave from the region of interest (ROI) in the heart wall based on the received plurality of wave signals; and a detecting means for detecting a variation frequency of the measured plurality of backscattering intensity signals during one pulsation of the heart to obtain the diagnostic data, said variation frequency being a frequency of tens to hundreds of Hz and being superimposed over heart cyclic variations (CV).

2. The ultrasonic diagnostic system according to claim 1, further comprising:

means for displaying in an assessable manner an instantaneous thickness variation velocity of the region of interest on a basis of the variation frequency or the variation cycle of the detected backscattering intensity.

3. The ultrasonic diagnostic system according to claim 2, wherein the means for displaying has a function to convert the variation frequency or the variation cycle of the backscattering intensity of the region of interest into a suitable color or a density level according to a predetermined color bar or gray scale, and a function to display it in the converted form on a screen.

4. The ultrasonic diagnostic system according to claim 3, wherein the function to display is to display superimposed over an M-mode image the value of the variation frequency or the variation cycle of the backscattering intensity converted into a color or a density level.

5. An ultrasonic diagnostic method for preparing a diagnostic data including image by transmitting ultrasonic pulses to a living tissue, and receiving and analyzing reflected wave of the ultrasonic pulses, the ultrasonic diagnostic method comprising:

transmitting an ultrasonic beam having a plurality of ultrasonic pulses to a living tissue while successively changing over radiating position of said ultrasonic beam, said plurality of ultrasonic pulses being transmitted at a repeated transmission frequency of a few kHz, said living tissue being a heart wall;

receiving a plurality of wave signals which are reflected at the heart wall;

measuring a plurality of backscattering intensity signals in one pulsation of a heart by using a scattering wave from a region of interest (ROI) in the heart wall based on the received plurality of wave signals; and detecting a variation frequency of the measured plurality of backscattering intensity signals in one pulsation of the heart to obtain the diagnostic data, said variation frequency being a frequency of tens to hundreds of Hz and being superimposed over cyclic variations (CV);

wherein the measuring step further comprises:

calculating a displacement waveform of the region of interest (ROI) by applying a phased tracking method to the received plurality of wave signals;

changing a position and size of the region of interest (ROI) based on the calculated displacement waveform; and calculating the plurality of backscattering intensity signals in one pulsation of the heart.

6. The ultrasonic diagnostic method according to claim 5, wherein an instantaneous thickness variation velocity of the region of interest is displayed in an assessable manner on a basis of the variation frequency or the variation cycle of the detected backscattering intensity.

7. The ultrasonic diagnostic method according to claim 6, wherein the variation frequency or the variation cycle of the backscattering intensity of the region of interest is converted into a suitable color or a density level according to a predetermined color bar or gray scale and is displayed in the converted form on a screen, in order to display in an assessable manner the instantaneous thickness variation velocity of the region of interest.

8. The ultrasonic diagnostic method according to claim 7, wherein the value of the variation frequency or the variation cycle of the backscattering intensity converted into a color or a density level is displayed by superimposing over an M-mode image.

9. An ultrasonic diagnostic method for preparing a diagnostic data, the ultrasonic diagnostic method comprising:

providing an ultrasonic diagnostic system;

providing a means for displaying an image;

transmitting an ultrasonic beam to a living tissue via said ultrasonic diagnostic system, said living tissue being a heart wall, said ultrasonic beam having a plurality of ultrasonic pulses, said plurality of ultrasonic pulses reflecting off said heart wall, said plurality of ultrasonic pulses being transmitted at a repeated transmission frequency of at least one kHz, said ultrasonic diagnostic system receiving said reflected plurality of ultrasonic pulses;

changing successively the radiating position of said ultrasonic beam via said ultrasonic diagnostic system;

calculating a displacement waveform of a region of interest (ROI) by applying a phased tracking method to the received plurality of wave signals, changing a position and size of the region of interest (ROI) based on the calculated displacement waveform and calculating the plurality of backscattering intensity signals in one pulsation of the heat for measuring a plurality of backscattering intensity signals in one pulsation of the heart by using a scattering wave from the region of interest (ROI) in the heart wall based on intensity of said received plurality of ultrasonic pulses; and detecting a variation frequency of the measured plurality of backscattering intensity signals in one pulsation of the heart to obtain the diagnostic data, said variation frequency being a frequency of tens to hundreds of Hz and being superimposed over the cyclic variations (CV).

* * * * *